US006777202B2

(12) United States Patent
Lubitz et al.

(10) Patent No.: US 6,777,202 B2
(45) Date of Patent: Aug. 17, 2004

(54) RECOMBINANT EXPRESSION OF S-LAYER PROTEINS

(75) Inventors: Werner Lubitz, Schönborngasse 12/7, A-1080 Wien/Vienna (AT); Uwe Sleytr, Wien/Vienna (AT); Beatrix Kuen, Wien/Vienna (AT); Michaela Truppe, Luftenberg (AT); Stefan Howorka, Wien/Vienna (AT); Stepanka Resch, Wien/Vienna (AT); Gerhard Schroll, Wien/Vienna (AT); Margit Sara, Gänserndorf (AT)

(73) Assignees: Werner Lubitz, Vienna (AT); NANO-S Biotechnologie GmbH, Vienna (AT)

( * ) Notice: Subject to any disclaimer, the term of this patent is extended or adjusted under 35 U.S.C. 154(b) by 0 days.

(21) Appl. No.: 09/117,447
(22) PCT Filed: Jan. 31, 1997
(86) PCT No.: PCT/EP97/00432
§ 371 (c)(1),
(2), (4) Date: Dec. 2, 1998
(87) PCT Pub. No.: WO97/28263
PCT Pub. Date: Aug. 7, 1997

(65) Prior Publication Data
US 2002/0168728 A1 Nov. 14, 2002

(30) Foreign Application Priority Data
Feb. 1, 1996 (DE) .......................... 196 03 649

(51) Int. Cl.$^7$ .......................... C12P 21/26; C12P 21/02; C12P 21/04; C12N 1/20; C07H 21/04
(52) U.S. Cl. .................. 435/69.1; 435/320.1; 435/69.3; 435/69.5; 435/69.7; 435/70.1; 435/71.1; 435/252.3; 435/71.2; 536/23.1; 536/23.5; 536/23.6
(58) Field of Search .............................. 536/23.1, 23.5, 536/23.6; 435/69.1, 320.1, 69.3, 69.5, 69.7, 70.1, 71.1, 252.3, 71.2

(56) References Cited

U.S. PATENT DOCUMENTS

| | | | |
|---|---|---|---|
| 5,470,573 A | * | 11/1995 | Lubitz et al. |
| 5,500,353 A | * | 3/1996 | Smit et al. |
| 5,783,441 A | * | 7/1998 | Carl et al. |
| 5,874,267 A | * | 2/1999 | Deblaere et al. |
| 5,976,864 A | * | 11/1999 | Smit et al. |
| 6,210,948 B1 | * | 4/2001 | Smit et al. |
| 6,596,510 B1 | * | 7/2003 | Lubitz et al. ............ 435/69.1 |
| 6,610,517 B1 | * | 8/2003 | Lubitz ...................... 435/70.1 |

FOREIGN PATENT DOCUMENTS

| | | | |
|---|---|---|---|
| DE | 44 25 527 | | 1/1996 |
| DE | 19603649 | * | 8/1997 |
| DE | 19732829 | * | 2/1999 |
| WO | 9519371 | * | 7/1995 |
| WO | 9728263 | * | 8/1997 |
| WO | 9906567 | * | 2/1999 |
| WO | 9734000 | * | 9/1999 |
| WO | 0004170 | * | 1/2000 |

OTHER PUBLICATIONS

Bowditch et al, J. Bacteriology, 1989, 171/8: 4178–4188.*
Yang et al, J. Bacteriology; 174/4:1258–1267, 1992.*
Miyamoto et al, FEMS Microbiology Letters, 116: 13–18, 1994.*
Peyret et al, Molecular Microbiology 9/1: 97–109, 1993.*
Jaresch et al, Microbiology, 2000 146: 273–281.*
Palva et al Med. Fac. Landbouww. Univ. Gent. 57/4b : 1891–1898, 1992.*
Kuen et al, Mal.Microbiology, 19/3:495–503, 1995.*
Kuen et al, Gene, 145:115–120, 1994.*
Bahl et al, FEMS Microbiol Rev. 20:47–98, 1997.*
Kuen et al, J. Bacteriol., 179/5:1664–1670, 1997.*
Savijoki et al, Gene 186: 255–262, 1997.
Howorka et al, FEMS Microbiol Lett. 172:187–196, 1999.
Scholz et al, Arch. Microbiol, 174: 97–103, 2000.
Bingle et al, Mol. Microbiol, 26/2:277–288, 1997.
International Publication No. WO 95/19371 published Jul. 20, 1995.
Bingle et al Canadian Jouirnal of Microbiology, vol. 40, No. 9, Sep. 1994, pp. 777–782, "Alkaline phosphatase and a cellulase reporter protein are not exported from the cytoplasm when fused . . . ".
Molecular Mirobiology, vol. 9, No. 1, 1993, pp. 97–109, "characterization of the cspB gene encloding PS2, an ordered surface–layer protein in *Corynebacterium glutamicum*". Peyret et al.
International Publication No. WO 91/13155 published Sep. 5, 1991.
Gene, vol. 145, No. 1, 1994, pp. 115–120, "Sequence analysis of te sbsA gene encoding the 130–kDa surface––layer protein of *bacillus stearothermophilus* strain PV72.", Kuen et al.
Journal of Bacteriology, vol. 176, No. 176, No. 23, Dec. 1994, pp. 7182–7189, "Comparative studies of S–layer proteins from *Bacillus stearothermpohilus* strains expressed during growth . . . ". Sara et al.
Molecular Microbiology, vol. 19, No. 3, Feb. 1996, pp. 495–503, "Heterologous expression and self–assembly of the S–layer protein SbsA of *Bacillus stearothermophilus* in *Escherichia coli*". Kuen et al.
Journal of Bacteriology, vol. 179, No. 5, Mar. 1997, pp. 1664–1670, "Molecular characterization of the *Bacillus stearothermophilus* PV72 S–layer gene sbsB induced . . . ".
TIBTECH, vol. 15, No. 1, Jan. 1997, pp. 20–26, "Bacterial and archaeal S–layer proteins: structure–function relationships and their biotechnological applications".

* cited by examiner

Primary Examiner—N. M. Minnifield
(74) Attorney, Agent, or Firm—Rothwell, Figg, Ernst & Manbeck P.C.

(57) ABSTRACT

The invention concerns a process for the recombinant production of S-layer proteins in gram-negative host cells. Furthermore the nucleotide sequence of a new S-layer gene and processes for the production of modified S-layer proteins are disclosed.

29 Claims, 3 Drawing Sheets

A)

B)

C)

A)

B)

C)

D)

E)

RECOMBINANT EXPRESSION OF S-LAYER PROTEINS

The present invention concerns processes for the recombinant production of S-layer proteins and modified S-layer proteins in gram-negative host cells.

Crystalline bacterial cell surface layers (S-layers) form the outermost cell wall component in many eubacteria and most of the archaebacteria (Sleytr et al. (1988), Crystalline Bacterial Cell Surface Layers, "Springer Verlag Berlin"; Messner and Sleytr, Adv. Microb. Physiol. 33 (1992), 213–275). Most of the presently known S-layer proteins are composed of identical proteins or glycoproteins which have apparent molecular weights in the range of 40,000 to 220,000. The components of S-layers are self-assembling and most of the lattices have an oblique (p2), quadratic (p4) or hexagonal (p6) symmetry. The functions of bacterial S-layers are still not completely understood but due to their location on the cell surface the porous crystalline S-layers probably serve mainly as protective coatings, molecular sieves or to promote cell adhesion and surface recognition.

Genetic data and sequence information are known for various S-layer genes from microorganisms. A review may be found in Peyret et al., Mol. Microbiol. 9 (1993), 97–109. Explicit reference is made to these data. The sequence of the sbsA gene coding for the S-layer protein of B.stearothermophilus PV72 and a process for cloning it are stated in Kuen et al. (Gene 145 (1994), 115–120). B.stearothermophilus PV72 is a gram-positive bacterium which is covered with a hexagonally arranged S-layer. The main component of the S-layer is a 128 kd protein which is the most frequent protein in the cell with a proportion of about 15% relative to the total protein components. Various strains of B.stearothermophilus have been characterized which differ with regard to the type of the S-layer lattice, the molecular weight and glycosilation of the S-layer components (Messner and Sleytr (1992), supra).

The German Patent Application P 44 25 527.6 discloses the signal peptide-coding section of the S-layer gene from B.stearothermophilus and the amino acid sequence derived therefrom. The cleavage site between the signal peptide and the mature protein is located between position 30 and 31 of the amino acid sequence. The signal peptide-coding nucleic acid can be operatively linked to a protein-coding nucleic acid and can be used for the recombinant production of proteins in a process in which a transformed host cell is provided, the host cell is cultured under conditions which lead to an expression of the nucleic acid and to production and secretion of the polypeptide coded thereby and the resulting polypeptide is isolated from the culture medium. Prokaryotic organisms are preferably used as host cells in particular gram-positive organisms of the genus bacillus.

Surprisingly it was found that the recombinant production of S-layer proteins is not only possible in gram-positive prokaryotic host cells but also in gram-negative prokaryotic host cells. In this case the S-layer protein is not formed in the interior of the host cell in the form of ordered inclusion bodies but rather unexpectedly in the form of ordered monomolecular layers.

Hence one subject matter of the present invention is a process for the recombinant production of S-layer proteins characterized in that (a) a gram-negative prokaryotic host cell is provided which is transformed with a nucleic acid coding for an S-layer protein selected from (i) a nucleic acid which comprises the nucleotide sequence shown in SEQ ID NO. 1 from position 1 to 3684 optionally without the section coding for the signal peptide, (ii) a nucleic acid which comprises a nucleotide sequence corresponding to the nucleic acid from (i) within the scope of the degeneracy of the genetic code and (iii) a nucleic acid which comprises a nucleotide sequence which hybridizes with the nucleic acids from (i) or/and (ii) under stringent conditions; (b) the host cell is cultured under conditions which lead to an expression of the nucleic acid and to production of the polypeptide coded thereby and (c) the resulting polypeptide is isolated from the host cell.

The term "stringent hybridization" is understood within the sense of the present invention to mean that a hybridization still also occurs after washing at 55° C., preferably 60° C. in an aqueous low salt buffer (e.g. 0.2× SSC) (see also Sambrook et al. (1989), Molecular Cloning. A Laboratory Manual).

The process according to the invention is carried out in gram-negative prokaryotic host cells. In this process an ordered S-layer protein structure is surprisingly obtained in the cell interior. Enterobacteria, in particular E. coli, are preferably used as host cells.

The E. coli strain pop2135 which was deposited on 31.01.1996 at the "Deutsche Sammlung von Mikroorganismen und Zelikulturen GmbH", Mascheroder Weg 1b, D 38124 Braunschweig under the file number DSM 10509 is particularly preferred The process according to the invention can also be used to isolate recombinant S-layer proteins. For this one uses a nucleic acid coding for the S-layer protein which contains one or several insertions which code for peptide or polypeptide sequences. These insertions can, on the one hand, only code for peptides with a few amino acids e.g. 1–25 amino acids. On the other hand, the insertions can also code for larger polypeptides of for example up to 1000 amino acids and preferably up to 500 amino acids without loss of the ability of the S-layer protein to form a correctly folded structure. In addition to the insertions the recombinant S-layer protein can also have amino acid substitutions, in particular substitutions of individual amino acids in the region of the insertion sites as well as optionally deletions of individual amino acids or short amino acid sections of up to 30 amino acids.

Regions between the positions 1–1200 and 2200–3000 of the nucleotide sequence shown in SEQ ID NO.1 are preferred as insertion sites for polypeptide-coding sequences. Particularly preferred insertion sites are the NruI cleavage site at position 582, the PvuII cleavage site at position 878, the SnaB-I cleavage site at position 917, the PvuII cleavage site at position 2504 and the PvuII cleavage site at position 2649. It was already possible to demonstrate the insertion of a nucleic acid coding for streptavidin into the NruI cleavage site at position 581.

The peptide or polypeptide-coding insertions are preferably selected from nucleotide sequences which code for cysteine residues, regions with several charged amino acids, e.g. Arg, Lys, Asp or Glu, or Tyr residues, DNA-binding epitopes, antigenic, allergenic or immunogenic epitopes, metal-binding epitopes, streptavidin, enzymes, cytokines or antibody-binding proteins.

A particularly preferred example of an insertion into the nucleic acid coding for the S-layer protein is a nucleotide sequence coding for streptavidin. In this manner it is possible to obtain universal carrier molecules which are suitable for coupling biotinylated reagents and for detection in immunological or hybridization test procedures.

A further preferred example of insertions are antigenic, allergenic or immunogenic epitopes e.g. epitopes from pathogenic microorganisms such as bacteria, fungi, parasites etc. and viruses, or epitopes from plants or epitopes against endogenous substances e.g. cytokines as well as against toxins in particular endotoxins. Particularly preferred examples of immunogenic epitopes are epitopes from herpes viruses such as the herpes virus 6 or pseudorabies virus (Lomniczi et al., J. Virol. 49 (1984), 970–979), in particular epitopes from the genes gB, gC or/and gD, or foot-and-mouth disease virus (FMDV), in particular epitopes from the gene sections which code for VP1, VP2 or/and VP3. The immunogenic epitopes can be selected such that they promote an antibody-mediated immune reaction or/and the production of a cellular immune reaction e.g. by stimulation of T cells. Examples of suitable allergenic epitopes are birch pollen allergens e.g. Bet v I (Ebner et al., J. Immunol. 150 (1993) 1047–1054). Antigenic epitopes are additionally particularly preferred which are able to bind and filter out endogenous or exogenous substances such as cytokines or toxins from serum or other body fluids. Such epitopes can include components of cytokine or toxin receptors or of antibodies against cytokines or toxins.

On the other hand the insertions can also code for enzymes. Preferred examples are enzymes for the synthesis of polyhydroxybutyric acid e.g. PHB synthase. Incorporation of PHB synthase into the S-layer can lead to the formation of a molecular spinning nozzle under suitable conditions when the substrate hydroxybutyric acid is provided. A further preferred example of an enzyme is bacterial luciferase. In this case when the enzyme substrate, an aldehyde, is supplied and 02 is present, a molecular laser can be obtained.

Insertions are likewise preferred which code for cytokines such as interleukins, interferones or tumour necrosis factors. These molecules can for example be used in combination with immunogenic epitopes to prepare vaccines.

Finally insertions are also preferred which code for antibody binding proteins such as protein A or protein G or for DNA-binding or/and metal-binding epitopes such as the leucine zipper, zinc finger etc.

Thus for the first time a cell is provided by the present invention which contains immobilized recombinant polypeptides in a native form e.g. active enzymes in the cytoplasm. In this manner 50,000–200,000 e.g. ca. 100,000 recombinant molecules can be immobilized per $m^2$ recombinant S-layer. Up to 3000 $m^2$ S-layer can be obtained per kg recombinant $E. coli$ cells.

In the method according to the invention the nucleic acid coding for the S-layer protein is preferably used in operative linkage with a nucleic acid coding for a signal peptide of gram-positive bacteria i.e. the signal peptide-coding nucleic acid is located on the 5' side of the S-layer protein-coding nucleic acid. Surprisingly it was found that the presence of such signal peptide sequences, which are not cleaved in the gram-negative host cells used in the invention, can improve the stability of the S-layer structures. The nucleic acid coding for the signal peptide particularly preferably comprises (a) the signal peptide-coding section of the nucleotide sequence shown in SEQ ID NO. 1, (b) a nucleotide sequence corresponding to the sequence from (a) within the scope of the degeneracy of the genetic code or/and (c) a nucleotide sequence which is at least 80% and in particular at least 90% homologous to the sequences from (a) or/and (b).

Yet a further subject matter of the present invention is a nucleic acid which codes for a recombinant S-layer protein and is selected from (i) a nucleic acid which comprises the nucleotide sequence shown in SEQ ID NO.1 from position 1 to 3684 optionally without the signal peptide-coding section (ii) a nucleic acid which comprises a nucleotide sequence corresponding to a nucleic acid from (i) within the scope of the degeneracy of the genetic code and (iii) a nucleic acid which comprises a nucleotide sequence which hybridizes under stringent conditions with the nucleic acids from (i) or/and (ii).

The coding nucleotide sequence of the S-layer gene sbsA from B.stearothermophilus including the signal peptide-coding section is shown in SEQ ID NO. 1. The signal peptide-coding section extends from position 1 to 90 of the nucleotide sequence shown in SEQ ID NO. 1. The section coding for the mature SbsA polypeptide extends from position 91 to 3684.

The sbsA gene of B.stearothermophilus codes for a protein with a total of 1228 amino acids including an N-terminal signal peptide with 30 amino acids (SEQ ID NO. 2). The cleavage site between the signal peptide and the mature protein is located between position 30 and 31 of the amino acid sequence. The signal peptide has a basic amino-terminal domain followed by a hydrophobic domain.

Sequence comparisons with other signal peptides indicate a certain homology to signal peptides of extracellular proteins in bacilli such as alkaline phosphatase and neutral phosphatase of B.amyloliquefaciens (Vasantha et al., J. Bacteriol. 159 (1984), 811–819) as well as with the signal peptides for the B.sphaericus gene 125 (Bowditch et al., J. Bacteriol. 171 (1989), 4178–4188) and the OWP qene of B.brevis (Tsuboi et al., J. Bacteriol. 168 (1986), 365–373).

A further subject matter of the present invention is a recombinant vector which contains at least one copy of a nucleic acid according to the invention. The vector is preferably replicatable in prokaryotes. The vector is particularly preferably a prokaryotic plasmid.

Yet a further subject matter of the present invention is a host cell which is transformed with a nucleic acid or a recombinant vector according to the present invention. The cell is preferably a gram-negative prokaryotic organism and most preferably an $E. coli$ cell. The cell according to the invention can contain a recombinant S-layer structure in its interior. Methods for the transformation of cells with nucleic acids are general state of the art (cf. Sambrook et al., supra) and therefore do not need to be elucidated.

Yet a further subject matter of the present invention is a recombinant S-layer protein which contains at least one peptide insertion or/and polypeptide insertion within the amino acid sequence shown in SEQ ID NO. 2. Preferred examples of peptide insertions and polypeptide insertions have already been elucidated.

A recombinant S-layer structure can be assembled from recombinant S-layer protein molecules according to the invention which contain at least one recombinant S-layer protein according to the invention as a subunit. Furthermore it is preferred that the S-layer structure according to the invention also contains non-modified S-layer proteins as diluent molecules. The non-modified S-layer proteins are preferably present in a molar proportion of 10–99% relative to the total S-layer proteins.

The S-layer structure according to the invention can comprise several layers that are covalently linked together or by means of affinity binding. Covalent linkages can for example be introduced by insertions of cysteine residues and a subsequent formation of cystine bridges. Linkages by affinity binding comprise for example antibody-antigen, antibody-protein A or antibody-protein G or streptavidin-biotin interactions.

S-layer structures which contain recombinant S-layer proteins can optionally also be prepared in a carrier-bound form. For this the S-layer structure can be reassembled from individual units in the presence of a peptidoglycan carrier to for example produce peptido-glycan layers which are coverged on one or on both sides with an S-layer structure. Another method of preparing carrier-bound S-layer structures is to produce an S-layer layer at an interface between two media e.g. water/air and to immobilize this layer on a solid phase e.g. a filter membrane (cf. e.g. Pum and Sleytr (1994), Thin Solid Films 244, 882–886; Kupcu et al., (1995), Biochim. Biophys. Acta 1235, 263–269).

The recombinant S-layer proteins and S-layer structures according to the invention are suitable for a multitude of applications. An application as a vaccine or adjuvant is particularly preferred in which case recombinant S-layer proteins are used which contain immunogenic epitopes of pathogens and/or endogenous immuno-stimulatory polypeptides such as cytokines. In this application it is not absolutely necessary to purify the recombinant S-layer proteins. Instead they can for example be used in combination with a bacterial ghost which optionally contains additional immunogenic epitopes in its membrane.

The preparation of suitable "bacterial ghosts" is described for example in the International Patent application PCT/EP91/00967 to which reference is herewith made. In this application modified bacteria are disclosed which are obtainable by transformation of a gram-negative bacterium with the gene of a lytically active membrane protein from bacteriophages, with the gene of a lytically active toxin release protein or with genes which contain partial sequences thereof which code for lytic proteins, culturing the bacterium, expression of this lysis gene and isolation of the resulting bacterial ghost from the culture medium.

A recombinant protein, which is obtainable by expression of a recombinant DNA in these gram-negative bacteria, can be bound to the membrane of these bacteria as described in the European Patent 0 516 655. This recombinant DNA comprises a first DNA sequence which codes for a hydrophobic, non-lytically active membrane-integrating protein domain which has an a-helical structure and is composed of 14–20 amino acids which can be flanked N- and C-terminally by 2–30 arbitrary amino acids in each case. A second DNA sequence is in operative linkage with this first DNA sequence which codes for a desired recombinant protein. Furthermore the gram-negative bacterium contains a third DNA sequence which is under a different control from the first and second DNA sequences and codes for a lytically active membrane protein from bacteriophages or a lytically active toxin release protein or for their lytically active components. So-called "bacterial ghosts" are obtained by expression and lysis of such recombinant gram-negative bacteria which contain an intact surface structure with immunogenic epitopes bound to the surface.

When these bacterial ghosts are combined with recombinant S-layers according to the invention vaccines and adjuvants can be produced which have particularly advantageous properties.

A further particularly preferred application for recombinant S-layer proteins and S-layer structures is their use as an enzyme reactor. Such an enzyme reactor can for example be formed by a cell which contains a recombinant S-layer structure according to the invention in its interior. On the other hand the enzyme reactor can also be formed from isolated and in vitro reassembled S-layer structures or combinations of various S-layer structures.

It was found that the gram-positive bacterium B.stearothermophilus PV72 has an additional S-layer protein in addition to SbsA which is subsequently denoted as SbsB (Sara and Sleytr (1994), J. Bacteriol. 176, 7182–7189). It was possible to isolate and characterize the sbsB gene by amplification using suitable nucleic acid primers. The coding nucleotide sequence of the S-layer gene sbsB from B.stearothermophilus including the signal peptide-coding section which extends from position 1 to 93 of the nucleic acid sequence is shown in SEQ ID NO.5. The amino acid sequence derived therefrom is shown in SEQ ID NO.6. The sbsB gene codes for a protein with a total of 921 amino acids including an N-terminal signal peptide with 31 amino acids.

One subject matter of the present invention is hence a nucleic acid which codes for an S-layer protein and is selected from (i) a nucleic acid which comprises the nucleotide sequence from position 1 to 2763 shown in SEQ ID NO.5 optionally without the signal peptide-coding section, (ii) a nucleic acid which comprises a nucleotide sequence corresponding to the nucleic acid from (i) within the scope of the degeneracy of the genetic code and (iii) a nucleic acid which comprises a nucleotide sequence that hybridizes with the nucleic acids from (i) or/and (ii) under stringent conditions.

As in the case of the sbsA gene, it is also possible to insert at least one nucleic acid insertion coding for a peptide or polypeptide into the sbsB gene within the region coding for the S-layer protein. With regard to preferred examples of insertions in the sbsB gene reference is made to the previous statements regarding the sbsA gene.

Yet a further subject matter of the present invention is a vector which contains at least one copy of an sbsB gene optionally containing an insertion. This vector can be replicated in eukaryotes, prokaryotes or in eukaryotes and prokaryotes. It can be a vector that can be integrated into the genome of the host cell or a vector which is present extrachromosomally. The vector according to the invention is preferably a plasmid in particular a prokaryotic plasmid.

Yet a further subject matter of the present invention is a host cell which is transformed with an sbsB gene wherein the sbsB gene optionally can contain an insertion. The host cell can be a eukaryotic as well as a prokaryotic cell. The cell is preferably a prokaryotic organism. Gram-positive organisms e.g. organisms of the genus bacillus as well as gram-negative organisms such as enterobacteria in particular *E. coli* are preferred. Methods for transforming eukaryotic and prokaryotic cells with nucleic acids are known and therefore do not need to be elucidated in detail.

The present invention also concerns an SbsB protein i.e. an S-layer protein which is coded by a nucleic acid as defined above. Recombinant SbsB proteins are particularly preferred which contain one or several peptide or/and polypeptide insertions within the sbsB sequence. The SbsB part of a polypeptide according to the invention particularly preferably has a homology of at least 80% and in particular of at least 90% to the amino acid sequence shown in SEQ ID NO.6.

A recombinant S-layer structure can also be assembled from the recombinant SbsB-S-layer protein molecules analogous to the recombinant SbsA-S-layer structure. In this structure the non-modified S-layer proteins are preferably present in a molar proportion of 10–99% relative to the total S-layer proteins.

The applications for the recombinant SbsB-S-layer proteins and S-layer structures according to the invention also correspond to the applications for SbsA mentioned above. In this connection its use as a vaccine or adjuvant or as an enzyme reactor is noteworthy.

Recombinant S-layer proteins are obtainable by a process in which (a) a host cell is provided which contains a nucleic acid coding for an S-layer protein which contains a peptide-coding or polypeptide-coding insertion within the region coding for the S-layer protein,
(b) the host cell is cultured under conditions which lead to an expression of the nucleic acid and to production of the polypeptide coded by it and
(c) the resulting polypeptide is isolated from the host cell or from the culture medium.

In a first preferred embodiment of this process a recombinant SbsA-S-layer protein is prepared i.e. the nucleic acid coding for the recombinant S-layer protein is selected from
(i) a nucleic acid which comprises the nucleotide sequence from position 1 to 3684 shown in SEQ ID NO.1 optionally without the signal peptide-coding section,
(ii) a nucleic acid which comprises a nucleotide sequence corresponding to the nucleic acid from (i) within the scope of the degeneracy of the genetic code and
(iii) a nucleic acid which comprises a nucleotide sequence which hybridizes with the nucleic acids from (i) or/and (ii) under stringent conditions.

In a second preferred embodiment a recombinant SbsB-S-layer protein is prepared i.e. the nucleic acid coding for the recombinant S-layer protein is selected from
(i) a nucleic acid which comprises the nucleotide sequence from position 1 to 2763 shown in SEQ ID NO.5 optionally without the signal peptide-coding section,
(ii) a nucleic acid which comprises a nucleotide sequence corresponding to the nucleic acid from (i) within the scope of the degeneracy of the genetic code and
(iii) a nucleic acid which comprises a nucleotide sequence which hybridizes with the nucleic acids from (i) or/and (ii) under stringent conditions.

In addition to the recombinant SbsA and SbsB-S-layer proteins from B.stearothermophilus it is, however, also possible to prepare recombinant S-layer proteins from other organisms (cf. e.g. Peyret et al., (1993), supra).

The recombinant S-layer proteins can on the one hand be produced in a heterologous host cell i.e. in a host cell which originally contains no S-layer gene. Examples of such heterologous host cells are gram-negative prokaryotic organisms such as *E. coli*.

However, the heterologous expression of S-layer proteins can also take place in gram-positive prokaryotic organisms such as *B. subtilis*. For this integration vectors are preferably used which contain a native or/and a recombinant S-layer gene. When the native signal sequences are used the S-layer proteins are secreted into the culture supernatant.

However, it is often preferable to produce the recombinant S-layer proteins in homologous host cells i.e. host cells which originally contain a natural S-layer gene. In one embodiment of this homologous expression the recombinant S-layer gene is introduced into the host cell in such a way that the host cell is still able to express a further S-layer gene which codes for a non-modified S-layer protein. The non-modified S-layer protein is preferably capable of forming an S-layer structure that is compatible with the recombinant S-layer protein. An example of this embodiment of homologous expression is a B.stearothermophilus PV72 cell which contains intact natural sbsA genes or/and sbsB genes and is transformed with a plasmid which contains a recombinant S-layer gene.

In a second embodiment the homologous expression can occur in a host cell in which the intact S-layer gene originally present has been inactivated. Consequently in this embodiment no further S-layer gene is expressed in the host cell which codes for a non-modified S-layer protein which is able to form a compatible S-layer structure with the recombinant S-layer protein. A specific example of such a host cell is a B.stearothermophilus PV72 cell in the genome of which a gene coding for a recombinant S-layer protein has been introduced, e.g. by homologous recombination, which replaces the original S-layer gene. A further example of such a host cell is a B.stearothermophilus cell in which the native S-layer gene has been inactivated e.g. by site-specific mutagenesis or/and homologous recombination and is transformed with a vector containing a recombinant S-layer gene.

Gram-positive prokaryotic organisms are usually used as host cells for the homologous expression of recombinant S-layer genes. B.stearothermophilus PV72 is particularly preferred as a host cell which can be cultured at a high temperature in a defined synthetic medium (Schuster et al., (1995), Biotechnol. and Bioeng. 48: 66–77).

The present invention is further elucidated by the following examples and figures.

SEQ ID NO.1 shows the complete nucleotide sequence of the coding section of the S-layer gene sbsA of B.stearothermophilus;

SEQ ID NO.2 shows the amino acid sequence derived therefrom;

SEQ ID NO.3 shows the nucleotide sequence of the primer T5-X;

SEQ ID NO.4 shows the nucleotide sequence of the primer E;

SEQ ID NO.5 shows the complete nucleotide sequence of the coding section of the S-layer gene sbsB of B.stearothermophilus;

SEQ ID NO.6 shows the amino acid sequence derived therefrom;

SEQ ID NO.7 shows the nucleotide sequence of a partial fragment of the streptavidin gene;

SEQ ID NO.8 shows the nucleotide sequence of the primer NIS 2AG;

SEQ ID NO.9 shows the nucleotide sequence of the primer LIS C3;

EXAMPLES

1. Bacterial Strains, Media and Plasmids

Figure 1:
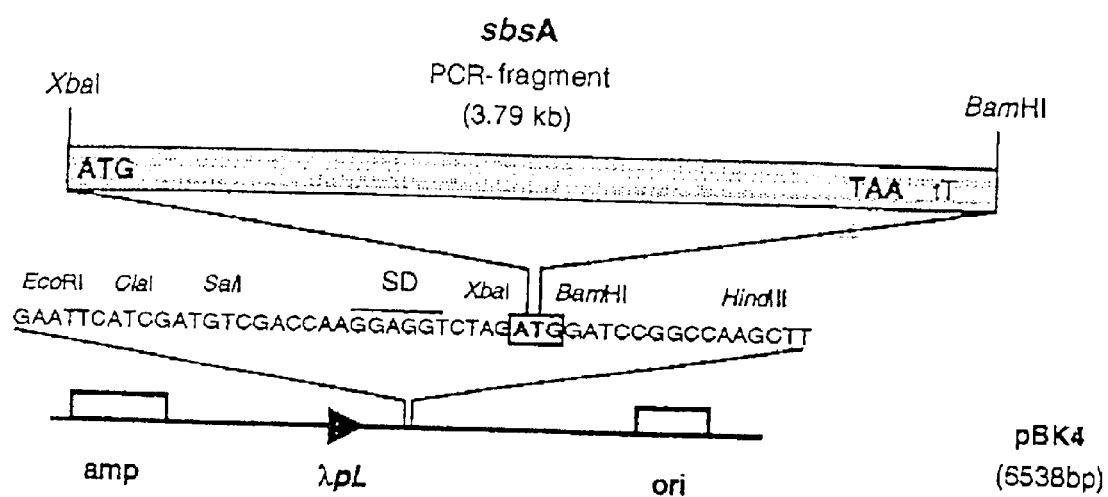
FIG. 1 shows a schematic representation of the sbsA PCR fragment used to prepare the recombinant vector pBK4.

Gram-positive bacteria of the strain Bacillus stearothermophilus PV72 were cultured at 58° C. in SVIII medium (Bartelmus and Perschak, Z. Zuckerrind. 7 (1957), 276–281). Bacteria of the strain *E. coli* pop2135 (endA, thi, hsdR, malT, cI857, XpR, malPQ) were cultured in LB medium (Sambrook et al., (1989), supra). Ampicillin was added to the medium at a final concentration of 100 µg/ml to select for transformants. The plasmid pPLcAT10 (kpL, bla, colEl) (Stanssens et al., Gene 36 (1985), 211–223) was used as the cloning vector.

2. Manipulation of DNA Fragments

Restriction analysis of DNA, agarose gel electrophoresis and cloning of DNA fragments were carried out according to the standard methods described in Sambrook et al. (1989), supra.

Competent cells were transformed by electroporation using a Bio-Rad gene pulser (Bio-Rad Laboratories, Richmond, Calif. USA) according to the manufacturer's instructions.

Plasmid DNA was isolated by the method of Birnboim and Doly (Nucleic Acids Res. 7 (1979), 1513–1523). Chromosomal DNA was isolated according to the method described in Ausubel et al. (Current Protocols in Molecular Biology (1987), N.Y., John Wiley).

Restriction endonucleases and other enzymes were obtained from Boehringer Mannheim, New England Biolabs or Stratagene and used according to the manufacturer's instructions.

3. DNA Sequencing

The DNA sequences of the 5' regions and the 3' regions (including the region coding for the signal sequence) of the gene sbsA in the vector pPLcAT10 were determined by the dideoxy chain termination method of Sanger et al. The primers used for sequencing were constructed on the basis of the already published sbsA sequence (Kuen et al. Gene 145 (1994), 115–120).

4. PCR Amplification of sbsA

The PCR amplification of the sbsA gene was carried out in a reaction volume of 100 $\mu$l in which 200 $\mu$M deoxynucleotides, 1 U Pfu-polymerase (Stratagene), 1× Pfu-reaction buffer, 0.5 $\mu$M of each oligonucleotide primer and 100 ng genomic DNA from B.stearothermophilus as a template were present. The amplification was carried out for 30 cycles in a thermocycler (Biomed thermocycler 60). Each cycle was composed of a denaturing step of 1.5 min at 95° C., an annealing step of 1 min at 56° C. and 1 min at 50° C. as well as an extension step of 2 min at 72° C.

The primer T5-X shown in the sequence protocol as SEQ ID NO.3 which flanks the 5' region of sbsA and contains an XbaI site and the primer E shown in the sequence protocol in SEQ ID NO.4 which flanks the 20 nucleotide upstream region of the transcription terminator of the sbsA sequence and contains a BamHI site were used as primers.

The products amplified by PCR were electrophoretically separated on a 0.8% agarose gel and purified for cloning using the system from Gene Clean (BIO101 La Jolla, Calif. USA).

5. Cloning of the sbsA Gene into the Vector pPLcAT10

The sbsA gene obtained by PCR with a length of 3.79 kb was purified and cleaved with the restriction endonucleases XbaI and BamHI. The resulting XbaI-BamHI fragment was cloned into the corresponding restriction sites of the vector pPLcAT10 so that the sbsA gene was under transcriptional control of the pL promoter located upstream. The ATG start codon of the sbsA sequence was reconstructed by the cloning procedure. The cloned sbsA sequence contained the N-terminal signal sequence of sbsA and ended 20 nt after the transcription terminator. After ligation of the vector DNA with the sbsA fragment, the E. coli strain pop2135 was transformed by electro-transformation. The resulting clones were subjected to a DNA restriction analysis. A positive clone was sequenced in order to verify the correct sequence transitions at the 5' and 3' ends. This clone was named pBK4.

A schematic representation of the 3.79 kb XbaI sbsA fragment and its location in the multiple cloning site of the plasmid pBK4 is shown in FIG. 1 (abbreviations: tT: transcription terminator; ori: origin of the DNA replication; amp: ampicillin resistance gene).

6. Recombinant Expression of the sbsA Gene in E. coli

E. coli pop2135/pBK4 cells were cultured at 28° C. until an optical density $OD_{600}$ of 0.3 was reached. Then the expression of sbsA was induced by increasing the culture temperature from 28° C. to 42° C. 1.5 ml aliquots were taken before and 1, 2, 3 and 5 hours after induction of the sbsA expression. E. coli pop2135/pPLcAT10 (cultured under the same conditions) and B.stearothermophilus PV72 were used as controls.

Culture supernatants and cell extracts from all samples were examined for the expression of S-layer proteins by SDS-PAGE and Western immunoblotting.

An additional strong protein band with the same molecular weight as the wild type SbsA protein was found in extracts from E. coli cells transformed with pBK4. No degradation products of SbsA itself were found in a period of up to 5 hours after induction of expression. Thus presumably the S-layer protein sbsA is stable in E. coli and is not degraded by proteases.

A densitometric determination of the relative amount of SbsA protein was carried out. At a time point of 4 hours after induction the sbsA protein was in a proportion of ca. 16% relative to the total cellular protein.

The SbsA protein produced in E. coli migrated in the SDS gel slightly more slowly than the natural SbsA protein from B.stearothermophilus. Experiments to determine the N-terminal amino acid sequence of the SbsA protein by Edman degradation were not successful due to a blocking of the N-terminus. Thus presumably the signal sequence was not cleaved in E. coli.

A Western blot analysis of total cell extracts and culture supernatants of E. coli/pBK4 also only yielded a single sbsA-specific protein band with a slightly higher molecular weight than wild type SbsA protein from stearothermophilus.

For the Western blot the proteins were transferred onto a nitrocellulose membrane and incubated with a polyclonal antiserum against SbsA from rabbits. The preparation of this antiserum is described in Egelseer et al. (J. Bacteriol. 177 (1995), 1444–1451). A conjugate of goat anti-rabbit IgG and alkaline phosphatase was used to detect bound SbsA-specific antibodies.

No SbsA protein could be detected from supernatants from E. coli cells transformed with pBK4 even after induction of sbsA gene expression. This shows that SbsA is not exported into the surrounding medium.

7. Location and Organisation of the S-Layer Protein SbsA in the Cytoplasm of E. coli Cells of E. coli pop2135/pBK4 which were harvested from cultures 1, 2, 3 and 5 hours after induction of the S-layer protein expression were examined for the intracellular organisation of sbsA. Non-induced cells cultured at 28° C. and cells of B.stearothermophilus PV72 were examined as controls.

For this whole cells of both organisms were fixed and embedded in detection resin according to the method of Messner et al. (Int. J.Syst.Bacteriol. 34 (1984), 202–210). Subsequently ultrathin sections of the embedded preparations were prepared and stained with uranyl acetate.

The cytoplasm of non-induced E. coli cells exhibited the typical granular structure which did not change even when the OD of the suspensions increased. Longitudinal sections of E. coli cells which were harvested 1 hour after induction of the S-layer protein expression exhibited parallel, leaf-like structures in the cytoplasm. From cross sections it was apparent that these structures have a concentric arrangement.

The amount of leaf-like structures considerably increased between 1 and 2 hours after induction of the sbsA expression and afterwards remained essentially constant.

The sbsA protein recombinantly produced in E. coli could also be detected by immunogold labelling with sbsA-specific antibodies. An ordered structure of the recombinantly produced SbsA protein was also found with this detection method.

It was clearly apparent from these morphological data that the SbsA protein did not aggregate to form irregular inclusion bodies but rather formed monomolecular S-layer crystals. A remarkable property of the SbsA-S-layer layers assembled in *E. coli* was the concentric arrangement at defined distances. The presence of the signal sequence did not interfere with correct assembly.

Figure 2:
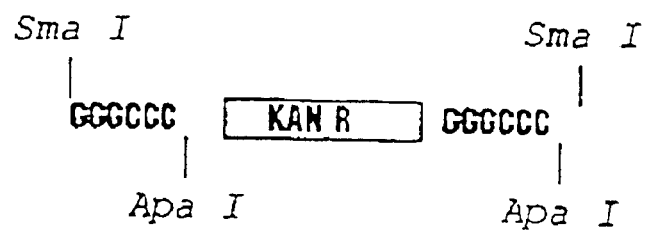
FIG. 2 shows a schematic representation of peptide insertions in the amino acid sequence of the SbsA S-layer protein and FIG. 3 shows a schematic representation of amino acid substitutions and amino acid insertions in recombinant S-layer proteins.
Figure 2:
Figure 2:

8. Preparation of Recombinant sbsA-S-Layer Genes 8.1 Insertion of a 6 bp Long DNA Sequence A modified kanamycin cassette (1.3 kb) was used for the site-specific insertion mutagenesis of the sbsA gene which was isolated by cleavage of the plasmid pWJC3 (obtained from W. T. McAllister, N.Y.) by SmaI. The cassette was ligated into five different blunt-ended restriction sites of the sbsA gene, i.e. into the NruI site at position bp 582 (pSL582), into the SnaBI site at position bp 917 (pSL917) and into each of the PvuII sites at positions bp 878 (pSL878), bp 2504 (pSL2504) and bp 2649 (pSL2649). After selection of kanamycin-resistant clones, the cassette was removed from the insertion site by cleavage with ApaI followed by a religation of the S-layer plasmid pBK4. The cutting out and religation procedure left an insertion of 6 bp CCCGGG (ApaI restriction site). The system of this linker insertion is shown schematically in FIG. 2.

The resulting recombinant S-layer genes code for modified sbsA proteins elongated by 2 amino acids.

Figure 3:
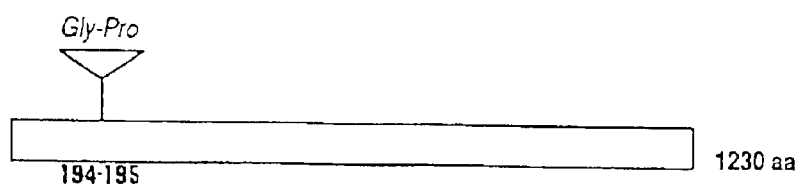
Figure 3:
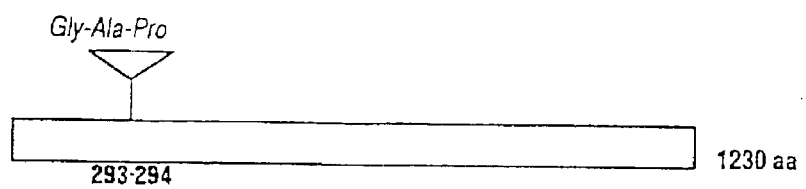
Figure 3:
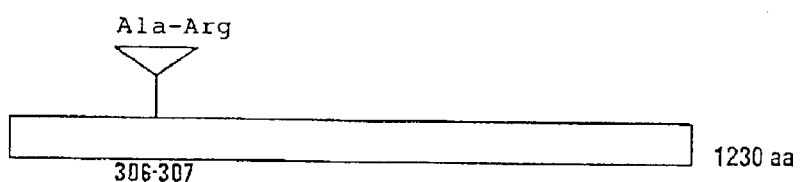
Figure 3:
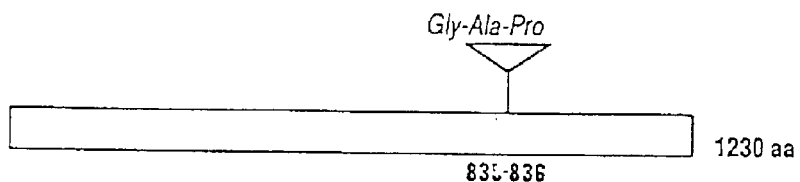
Figure 3:

The specific changes in the primary structure of the sbsA proteins are shown in FIG. 3. In the clone pSL582 the insertion led to the incorporation of glycine and proline between the amino acids 194 and 195 at the N-terminus of the SbsA protein. The amino acids alanine and arginine were inserted in the clone pSL917 between the amino acids 306 and 307. In the clone pSL2649 glycine and proline were inserted between the amino acids at positions 883 and 884. An insertion of alanine and proline between the amino acids 293 and 294 was obtained in the clone pSL878. Furthermore the alanine at position 293 was substituted by glycine. In the clone pSL2504 the amino acids alanine and proline were inserted between the amino acids 835 and 836 and the alanine at position 835 was replaced by glycine.

All clones obtained by insertion mutagenesis retained their ability to synthesise the S-layer protein.

In order to test the ability of the modified proteins to assemble into S-layer structures, ultrathin longitudinal sections of whole cells which had been cultured for 4 hours under inductive conditions were prepared according to the procedure described in section 7. It was found that the cytoplasm of all five clones is filled with parallel, leaf-like structures which follow the curve of the cell poles. There were no morphological differences of the cytoplasm in the 5 different clones examined. Exactly the same leaf-like structures were found as in the assembly of the wild type SbsA protein in *E. coli* (section 7).

8.2 Insertion of a DNA Sequence Coding for Streptavidin

In order to examine whether the insertion of larger protein sequences into the SbsA protein can also be tolerated, a DNA fragment coding for a part of streptavidin (160 amino acids) provided with ApaI linkers (SEQ ID NO.7) was gene inserted into the ApaI restriction site of the sbsA clones pSL582, pSL878, pSL917 and pSL2649 prepared in the example on page 1. The streptavidin sequence was inserted in SL582 in the codon 197, in pSL878 between codon 295 and 296, in pSL917 in the codon 308 and 309 and in pSL2649 in the codon 886. It was possible to detect the expression of SbsA-streptavidin fusion proteins in all constructs by SDS-PAGE and immunoblots. It was found by EM analysis that a self assembly of the S-layer structure was possible in the fusion proteins containing insertions in the codon 197 and between the codons 295 and 296.

The SbsA-streptavidin fusion proteins can be isolated as monomers and reassembled to form homogeneous SbsA-streptavidin S-layers or mixed SbsA-streptavidin/SbsA-S-layers. They can be used to bind biotinylated substances as well as to determine the binding capacity of enzymes and other bound molecules.

8.3 Insertion of a DNA Sequence Coding for BetvI

A DNA sequence coding for the open reading frame of BetvI (161 amino acids) the main pollen allergen of the birch (Ferreira et al., J. Biol. Chem. 268 (1993), 19574–19580) was inserted at the ApaI site into the sbsA clone pSL878. It was possible to detect the expression of an SbsA-BetvI fusion protein which contained an immunologically active BetvI domain.

The resulting fusion protein can be used for therapeutic or diagnostic purposes. Hence it can be attempted by administration of the fusion protein to convert a $TH^2$-directed IgE antibody reaction into a TH1-mediated reaction against BetvI. In this manner it is possible to suppress the occurrence of symptoms of a pollen allergy. Furthermore SbsA-BetvI fusion proteins can be used to test for anti-BetvI antibody concentrations or/and to reduce high concentrations of anti-BetvI IgE.

8.4 Insertion of a DNA Sequence Coding for a Pseudorabies Virus Antigen

The DNA sequence coding for the gB epitope SmaBB (255 amino acids) (nucleotides 489–1224 corresponding to the coordinates according to the EMBL-Seq: HEHSSGP2) from the pseudorabies virus was inserted into SSpI site of the sbsA gene after nt 3484 (between codon 1161 and 1162). It was possible to detect the expression of SbsA-SmaBB fusion proteins.

The fusion proteins can be used to test gB-specific immune reactions. A Western blot analysis using a monoclonal antibody which corresponds to the inserted sequence showed the immunological activity of the viral domain within the recombinant SbsA-SmaBB proteins.

8.5 Insertion of a DNA Sequence Coding for the PHB Synthase (PhbC) from *Alcaligenes eutrophus* H16

A regular arrangement of polypeptide structures with enzymatic activity on the surface of S-layers is an important goal in the production of immobilized enzymes within a living cell and in the case of the 590 amino acid long PHB synthase for the production of a molecular machine for biopolymer synthesis.

The phbc gene was isolated by PCR from the plasmid p4A (Janes et al., Molecular characterisation of the poly-β-hydroxy-butyrate biosynthesis in *Alcaligenes eutrophus* H16. In: Novel Biodegradable Microbial Polymers (publisher Daves, E. A.), pp 175–190 (1990), Kluver, Dordrecht) as a 1770 nt long DNA fragment (corresponding to an open reading frame of 590 amino acids) and inserted into the ApaI cleavage site of the sbsA clone pSL878 to obtain the plasmid pSbsA-PhbC. It was possible to detect the expression of an SbsA-PhbC fusion protein of ca. 195 kD in an *E. coli* cell transformed with this plasmid. When two copies of the phbc gene were inserted one behind the other into the ApaI site of pSL878, it was possible to detect the expression of a fusion protein of ca. 260 kD.

For a functional test of the enzymatic activity of the SbsA-PhbC construct, the *E. coli* cells which contained the plasmid pSbsA-PhbC were co-transformed with the plasmid pUMS which contains the β-ketothiolase (PhbA) and the acetoacetyl-CoA reductase (PhbB) from *A. eutrophus* (Kalousek et al., Genetic engineering of PHB-synthase from *Alcaligenes eutrophus* H16. In: Proceedings of the International Symposium on Bacterial Polyhydroxy-alkanoates, pp 426–427 (1993), publisher Schlegel H. G., Steinbuchel A. Goltze Press, Gbttingen). The poly-β-hydroxybutyrate formation in the co-transformed *E. coli* cells was detectable by staining with Sudan black, gas chromatography and electron microscopy. These findings show that the SbsA-PhbC construct is enzymatically active and represents a successful example of the immobilization of enzymes on intracellular S-layer matrices.

8.6 Insertion of a DNA Sequence Coding for a Bacterial Luciferase Gene

A monocistronic LuxAB gene with a length of 2,070 nt which contains the fusion protein LuxAB composed of the two subunits LuxB and LuxB of the bacterial luciferase from Vibrio harveyi was isolated from the plasmid pT7–mut3 (Boylan et al., J. Biol. Chem. 264 (1989), 1915–1918) by PCR and inserted into the ApaI site of the clone pSL878 prepared in example 8.1 to obtain the plasmid pBK878-LuxAB. It was possible to detect the expression of an SbsA-PhbC fusion protein of ca. 207 kD in an *E. coli* cell transformed with this plasmid. The enzymatic activity of the fusion protein was demonstrated by the method described in Boylan et al., Supra.

9. Isolation and Characterization of the sbsB Gene

The basis for the isolation of the sbsB gene was the amino acid sequence of the N-terminus as well as the sequence of three internal peptides of the SbsB protein. Starting with these peptide sequences, degenerate oligonucleotide primers were constructed and used for the PCR. In this manner a 1076 bp long PCR fragment from the chromosomal DNA of B.stearothermophilus was amplified, cloned and sequenced (corresponding to position 100–1176 of the sequence shown in SEQ ID NO.5).

The method of inverse PCR was used to amplify the sections on the 5' side and 3' side of the sbsB gene and stepwise overlapping DNA fragments were obtained with the aid of various primer combinations and sequenced.

The primer NIS 2AG shown in the sequence protocol as SEQ ID NO.8 which contains the 5' region of sbsB as well as the primer LIS C3 shown in the sequence protocol of SEQ ID NO.9 which contains the 3' region of sbsB were used as primers to amplify the complete sbsB gene.

The PCR fragment obtained in this manner which contains the nucleotide sequence shown in SEQ ID NO.5 with 5' and 3' BamHI restriction cleavage sites was cloned as described in example 5 into the vector pPLcAT10 in which the expression takes place under the control of the lambda PL promoter.

Furthermore the sbsB-PCR fragment with the 5' side EcoRI and 3' side BamHi cleavage site were cloned into the vector pUC18 in which the expression took place under the control of the lac promoter.

The detection of the sbsB expression was carried out as described in examples 6 and 7 by SDS gel electrophoresis and electron microscopy.

10. Preparation of Recombinant sbsB-S-Layer Genes

Recombinant sbsB genes were prepared analogously to the methods described in example 8.

Thus in accordance with the method described in example 8.1, a 6 nt long DNA sequence containing an ApaI restriction cleavage site was introduced at various positions into the sbsB-layer gene. The recombinant sbsB clones pAK407, pAK481 and pAK1582 with ApaI cleavage sites at nt 407 (codon 136), 481 (codon 161/162) and 1582 (codon 528/529) were obtained in this manner. These clones obtained by insertion mutagenesis retained their ability to synthesize the S-layer protein and form S-layer structures.

Analogously to the method described in example 8.2, a DNA fragment coding for streptavidin was inserted into the ApaI restriction sites of the sbsB clones pAK407 and pAK481.

Analogously to example 8.4, a DNA sequence coding for the gB epitope SmaBB was inserted into the ApaI cleavage sites of the sbsB clones pAK481 and pAK1582. It was possible to detect the expression of sbsB-SmaB fusion proteins of ca. 130 kD in the *E. coli* cells transformed with the resulting recombinant plasmids. When two copies of the SmaBB epitopes were inserted one behind the other into the ApaI cleavage site of pAK481 it was possible to detect the expression of a fusion protein of ca. 157 kD. The SmaBB domains of the fusion proteins were recognized by specific antibodies.

Analogously to example 8.6 it was possible to detect the expression of a 175 kD SbsB-LuxAB fusion protein when the LuxAB sequence was inserted into the ApaI cleavage site of pAK407.

11. Heterologous Expression of sbsA and sbsB in *Bacillus subtilis*

The integration vector pX (Kim, L., Mogk, A. and Schumann W., Gene 181 (1996), 71–76: A xylose-inducible *Bacillus subtilis* integration vector and its application) was used for the heterologous expression of sbsA and sbsB in *B. subtilis*. The S-layer genes in the resulting recombinant expression vectors are under the transcriptional control of the xyl promoter.

Transformants of *B.subtilis* containing an S-layer gene integrated in the chromosome exhibited an expression of large amounts of S-layer proteins in the supernatant of the cells which was inducible by addition of xylose to the growth medium. This shows that the signal sequences of sbsA and sbsB are recognized by the *B. subtilis* cell.

In an analogous manner it was possible to achieve a heterologous expression of recombinant sbsA and sbsB layer genes in *B. subtilis*.

What is claimed is:

1. A process for production of a crystalline S-layer protein comprising:
   (a) transforming a gram-negative prokaryotic host cell with a full length nucleic acid encoding an S-layer protein selected from the group consisting of
      (i) a nucleic acid comprising a nucleotide sequence from position 1 to 3684 of SEQ ID NO:1,
      (ii) a nucleic acid comprising a nucleotide sequence which encodes an amino acid sequence according to SEQ ID NO:2, and
      (iii) a nucleic acid comprising a nucleotide sequence which hybridizes with at least one of the nucleic acid of (i) or (ii) under stringent conditions;
   (b) culturing the host cell under conditions which induce expression of the nucleic acid and production of the corresponding protein, and
   (c) isolating the protein from the host cell.

2. The process as claimed in claim 1, wherein the gram-negative prokaryotic host cell is an *E. coli* host cell.

3. The process as claimed in claim 1, comprising isolating the protein from the interior of the host cell in the form of an assembled S-layer structure.

4. The process as claimed in claim 1, wherein the nucleic acid encoding the S-layer protein comprises at least one insertion encoding peptide or polypeptide sequences.

5. The process as claimed in claim 4, wherein the at least one insertion is a nucleotide sequence encoding a member selected from the group consisting of cysteine residues, regions with several charged amino acids or tyrosine residues, DNA-binding epitopes, metal-binding epitopes, immunogenic epitopes, allergenic epitopes, antigenic epitopes, streptavidin, enzymes, cytokines, and antibody-binding proteins.

6. The process as claimed in claim 5, wherein the at least one insertion encodes streptavidin.

7. The process as claimed in claim 5, wherein the at least one insertion encodes immunogenic epitopes from a herpes virus.

8. The process as claimed in claim 5, wherein the at least one insertion encodes enzymes comprising polyhydroxybutyric acid synthase or bacterial luciferase.

9. The process as claimed in claim 5, wherein the at least one insertion encodes cytokines comprising interleukins, interferons or tumour necrosis factors.

10. The process as claimed in claim 5, wherein the at least one insertion encodes antibody-binding proteins comprising protein A or protein G.

11. The process as claimed in claim 5, wherein the at least one insertion encodes antigenic epitopes which bind cytokines or endotoxins.

12. The process as claimed in claim 5, wherein the at least one insertion encodes metal-binding epitopes.

13. The process as claimed in claim 1, wherein a nucleic acid encoding a gram-positive signal peptide is arranged in operative linkage at the 5' side of the nucleic acid encoding the S-layer protein.

14. The process as claimed in claim 13, wherein the nucleic acid encoding the signal peptide comprises (a) a signal peptide coding region of the nucleotide sequence of SEQ ID NO:1, (b) a nucleotide sequence which encodes an amino acid sequence according to SEQ ID NO:2, or (c) a nucleotide sequence that is at least 80% homologous to at least one nucleotide sequence of (a) or (b).

15. An isolated nucleic acid encoding a full-length, crystalline recombinant S-layer protein selected from the group consisting of (i) a nucleic acid comprising a nucleotide sequence from position 1 to 3684 of SEQ ID NO:1, (ii) a nucleic acid comprising a nucleotide sequence which encodes an amino acid sequence according to SEQ ID NO:2, and (iii) a nucleic acid comprising a nucleotide sequence which hybridizes with at least one of the nucleic acid of (i) or (ii) under stringent conditions, wherein the nucleic acid contains at least one peptide or polypeptide-coding insertion within the region encoding the S-layer protein, wherein the insertion is a site located at position 582, 878, 917, 2504 or 2649 of the nucleotide sequence of SEQ ID NO. 1.

16. A vector comprising at least one copy of a nucleic acid as claimed in claim 15.

17. A transformed cell comprising a nucleic acid as claimed in claim 15 or a vector as claimed in claim 16, wherein the cell is a gram-negative prokaryotic cell.

18. A cell as claimed in claim 17, comprising a recombinant S-layer structure.

19. A transformed cell wherein the cell is transformed with a nucleic acid as claimed in claim 15.

20. A transformed cell wherein the cell is transformed with a vector as claimed in claim 16.

21. The process according to claim 1, wherein the nucleic acid of (i) does not contain a signal peptide-coding region.

22. The process according to claim 13 wherein said stringent conditions are washing at 55° C. in an aqueous low salt buffer comprising 0.2 ×SSC.

23. The process according to claim 22, wherein said stringent conditions are washing at 60° C. in an aqueous low salt buffer comprising 0.2 ×SSC.

24. The nucleic acid according to claim 15, wherein the nucleic acid of (i) does not contain a signal peptide-coding region.

25. The nucleic acid according to claim 15, wherein said stringent conditions are washing at 55° C. in an aqueous low salt buffer comprising 0.2 ×SSC.

26. The nucleic acid according to claim 25, wherein said stringent conditions are washing at 60° C. in an aqueous low salt buffer comprising 0.2 ×SSC.

27. The cell as claimed in claim 17, wherein the cell is *E. coli* in origin.

28. The process as claimed in claim 7, wherein the herpes virus comprises herpes virus 6 or FMDV.

29. A process for production of a crystalline S-layer protein comprising a) transforming a gram-negative prokaryotic host cell with a full-length nucleic acid encoding an S-layer protein which comprises at least one insertion encoding peptide or polypeptide sequences and selected from the group consisting of (i) a nucleic acid comprising a nucleotide sequence from position 1 to 3684 of SEQ ID NO.1, (ii) a nucleic acid comprising a nucleotide sequence which encodes the same amino acid sequence as the nucleic acid of (i), and (iii) a nucleic acid comprising a nucleotide sequence which hybridizes with at least one of the nucleic acids of (i) or (ii) under stringent conditions;

(b) culturing the host cell under conditions which induce expression of the nucleic acid and production of the corresponding protein, and (c) isolating the protein from the host cell.

* * * * *

SEQUENCE LISTING

```
<160> NUMBER OF SEQ ID NOS:  10

<210> SEQ ID NO 1
<211> LENGTH: 3687
<212> TYPE: DNA
<213> ORGANISM: Bacillus stearothermophilus
<220> FEATURE:
```

```
<221> NAME/KEY: CDS
<222> LOCATION: (1)..(3684)
<221> NAME/KEY: sig_peptide
<222> LOCATION: (1)..(90)
<221> NAME/KEY: mat_peptide
<222> LOCATION: (91)..(3684)

<400> SEQUENCE: 1 atg gat agg aaa aaa gct gtg aaa cta gca aca gca agt gct att gca        48
Met Asp Arg Lys Lys Ala Val Lys Leu Ala Thr Ala Ser Ala Ile Ala
-30             -25                 -20                 -15 gca agt gca ttt gtc gct gca aat cca aac gct tct gaa gcg gct aca        96
Ala Ser Ala Phe Val Ala Ala Asn Pro Asn Ala Ser Glu Ala Ala Thr
            -10                  -5                  -1   1 gat gta gca aca gta gta agc caa gca aaa gca cag ttc aaa aaa gca       144
Asp Val Ala Thr Val Val Ser Gln Ala Lys Ala Gln Phe Lys Lys Ala
              5                  10                  15 tac tat act tac agc cat aca gta acg gaa act ggt gaa ttc cca aac       192
Tyr Tyr Thr Tyr Ser His Thr Val Thr Glu Thr Gly Glu Phe Pro Asn
     20                  25                  30 att aac gat gta tat gct gaa tac aac aaa gcg aaa aaa cga tac cgt       240
Ile Asn Asp Val Tyr Ala Glu Tyr Asn Lys Ala Lys Lys Arg Tyr Arg
 35                  40                  45                  50 gat gcg gta gca tta gtg aat aaa gca ggt ggc gcg aaa aaa gac gct       288
Asp Ala Val Ala Leu Val Asn Lys Ala Gly Gly Ala Lys Lys Asp Ala
                 55                  60                  65 tac tta gct gat tta caa aaa gaa tat gaa act tac gtt ttc aaa gca       336
Tyr Leu Ala Asp Leu Gln Lys Glu Tyr Glu Thr Tyr Val Phe Lys Ala
             70                  75                  80 aac cct aaa tct ggc gaa gct cgt gta gca act tac atc gat gct tac       384
Asn Pro Lys Ser Gly Glu Ala Arg Val Ala Thr Tyr Ile Asp Ala Tyr
             85                  90                  95 aac tat gca aca aaa tta gac gaa atg cgc caa gag cta gag gct gct       432
Asn Tyr Ala Thr Lys Leu Asp Glu Met Arg Gln Glu Leu Glu Ala Ala
100                 105                 110 gtt caa gca aaa gat tta gaa aaa gca gaa caa tac tat cac aaa att       480
Val Gln Ala Lys Asp Leu Glu Lys Ala Glu Gln Tyr Tyr His Lys Ile
115                 120                 125                 130 cct tat gaa att aaa act cgc aca gtc att tta gat cgc gta tat ggt       528
Pro Tyr Glu Ile Lys Thr Arg Thr Val Ile Leu Asp Arg Val Tyr Gly
                135                 140                 145 aaa aca act cgt gat tta ctt cgc tct aca ttt aaa gca aaa gca caa       576
Lys Thr Thr Arg Asp Leu Leu Arg Ser Thr Phe Lys Ala Lys Ala Gln
            150                 155                 160 gaa ctt cgc gac agc tta att tat gat att acc gtt gca atg aaa gcg       624
Glu Leu Arg Asp Ser Leu Ile Tyr Asp Ile Thr Val Ala Met Lys Ala
            165                 170                 175 cgc gaa gta caa gac gct gtg aaa gca ggc aat tta gac aaa gct aaa       672
Arg Glu Val Gln Asp Ala Val Lys Ala Gly Asn Leu Asp Lys Ala Lys
        180                 185                 190 gct gct gtt gat caa atc aat caa tac tta cca aaa gta aca gat gct       720
Ala Ala Val Asp Gln Ile Asn Gln Tyr Leu Pro Lys Val Thr Asp Ala
195                 200                 205                 210 ttc aaa act gaa cta aca gaa gta gcg aaa aaa gca tta gat gca gat       768
Phe Lys Thr Glu Leu Thr Glu Val Ala Lys Lys Ala Leu Asp Ala Asp
                215                 220                 225 gaa gct gcg ctt act cca aaa gtt gaa agt gta agt gcg att aac act       816
Glu Ala Ala Leu Thr Pro Lys Val Glu Ser Val Ser Ala Ile Asn Thr
            230                 235                 240 caa aac aaa gct gtt gaa tta aca gca gta cca gtg aac gga aca cta       864
Gln Asn Lys Ala Val Glu Leu Thr Ala Val Pro Val Asn Gly Thr Leu
```

```
                      245                 250                 255
aaa tta caa ctt tca gct gct gca aat gaa gat aca gta aac gta aat     912
Lys Leu Gln Leu Ser Ala Ala Ala Asn Glu Asp Thr Val Asn Val Asn
    260                 265                 270 act gta cgt atc tat aaa gtg gac ggt aac att cca ttt gcc ctt aat     960
Thr Val Arg Ile Tyr Lys Val Asp Gly Asn Ile Pro Phe Ala Leu Asn
275                 280                 285                 290 acg gca gat gtt tct tta tct aca gac gga aaa act atc act gtg gat     1008
Thr Ala Asp Val Ser Leu Ser Thr Asp Gly Lys Thr Ile Thr Val Asp
                295                 300                 305 gct tca act cca ttc gaa aat aat acg gag tat aaa gta gta gtt aaa     1056
Ala Ser Thr Pro Phe Glu Asn Asn Thr Glu Tyr Lys Val Val Val Lys
            310                 315                 320 ggt att aaa gac aaa aat ggc aaa gaa ttt aaa gaa gat gca ttc act     1104
Gly Ile Lys Asp Lys Asn Gly Lys Glu Phe Lys Glu Asp Ala Phe Thr
        325                 330                 335 ttc aag ctt cga aat gat gct gta gtt act caa gtg ttt gga act aat     1152
Phe Lys Leu Arg Asn Asp Ala Val Val Thr Gln Val Phe Gly Thr Asn
    340                 345                 350 gta aca aac aac act tct gta aac tta gca gca ggt act ttc gac act     1200
Val Thr Asn Asn Thr Ser Val Asn Leu Ala Ala Gly Thr Phe Asp Thr
355                 360                 365                 370 gac gat act tta aca gta gta ttt gat aag ttg tta gca cct gaa act     1248
Asp Asp Thr Leu Thr Val Val Phe Asp Lys Leu Leu Ala Pro Glu Thr
                375                 380                 385 gta aac agc tcg aac gtt act att aca gat gtt gaa act gga aaa cgc     1296
Val Asn Ser Ser Asn Val Thr Ile Thr Asp Val Glu Thr Gly Lys Arg
            390                 395                 400 att cca gta att gca tct act tct ggt tct aca att act att acg tta     1344
Ile Pro Val Ile Ala Ser Thr Ser Gly Ser Thr Ile Thr Ile Thr Leu
        405                 410                 415 aaa gaa gcg tta gta act ggt aaa caa tat aaa ctt gct atc aat aat     1392
Lys Glu Ala Leu Val Thr Gly Lys Gln Tyr Lys Leu Ala Ile Asn Asn
    420                 425                 430 gtt aaa aca tta act ggt tac aat gca gaa gct tac gag tta gtg ttc     1440
Val Lys Thr Leu Thr Gly Tyr Asn Ala Glu Ala Tyr Glu Leu Val Phe
435                 440                 445                 450 act gca aac gca tca gca cca act gtt gct acc gct cct act act tta     1488
Thr Ala Asn Ala Ser Ala Pro Thr Val Ala Thr Ala Pro Thr Thr Leu
                455                 460                 465 ggt ggt aca act tta tct act ggt tct ctt aca aca aat gtt tgg ggt     1536
Gly Gly Thr Thr Leu Ser Thr Gly Ser Leu Thr Thr Asn Val Trp Gly
            470                 475                 480 aaa ttg gct ggt ggt gtg aat gaa gct gga act tat tat cct ggt ctt     1584
Lys Leu Ala Gly Gly Val Asn Glu Ala Gly Thr Tyr Tyr Pro Gly Leu
        485                 490                 495 caa ttc aca aca acg ttt gct act aag tta gac gaa tct act tta gct     1632
Gln Phe Thr Thr Thr Phe Ala Thr Lys Leu Asp Glu Ser Thr Leu Ala
    500                 505                 510 gat aac ttt gta tta gtt gaa aaa gaa tct ggt aca gtt gtt gct tct     1680
Asp Asn Phe Val Leu Val Glu Lys Glu Ser Gly Thr Val Val Ala Ser
515                 520                 525                 530 gaa cta aaa tat aat gca gac gct aaa atg gta act tta gtg cca aaa     1728
Glu Leu Lys Tyr Asn Ala Asp Ala Lys Met Val Thr Leu Val Pro Lys
                535                 540                 545 gcg gac ctt aaa gaa aat aca atc tat caa atc aaa att aaa aaa ggc     1776
Ala Asp Leu Lys Glu Asn Thr Ile Tyr Gln Ile Lys Ile Lys Lys Gly
            550                 555                 560 ttg aag tcc gat aaa ggt att gaa tta ggc act gtt aac gag aaa aca     1824
```

```
Leu Lys Ser Asp Lys Gly Ile Glu Leu Gly Thr Val Asn Glu Lys Thr
            565                 570                 575 tat gag ttc aaa act caa gac tta act gct cct aca gtt att agc gta   1872
Tyr Glu Phe Lys Thr Gln Asp Leu Thr Ala Pro Thr Val Ile Ser Val
580                 585                 590 acg tct aaa aat ggc gac gct gga tta aaa gta act gaa gct caa gaa   1920
Thr Ser Lys Asn Gly Asp Ala Gly Leu Lys Val Thr Glu Ala Gln Glu
595                 600                 605                 610 ttt act gtg aag ttc tca gag aat tta aat aca ttt aat gct aca acc   1968
Phe Thr Val Lys Phe Ser Glu Asn Leu Asn Thr Phe Asn Ala Thr Thr
                615                 620                 625 gtt tcg ggt agc aca atc aca tac ggt caa gtt gct gta gta aaa gcg   2016
Val Ser Gly Ser Thr Ile Thr Tyr Gly Gln Val Ala Val Val Lys Ala
            630                 635                 640 ggt gca aac tta tct gct ctt aca gca agt gac atc att cca gct agt   2064
Gly Ala Asn Leu Ser Ala Leu Thr Ala Ser Asp Ile Ile Pro Ala Ser
            645                 650                 655 gtt gaa gcg gtt act ggt caa gat gga aca tac aaa gtg aaa gtt gct   2112
Val Glu Ala Val Thr Gly Gln Asp Gly Thr Tyr Lys Val Lys Val Ala
            660                 665                 670 gct aac caa tta gaa cgt aac caa ggg tac aaa tta gta gtg ttc ggt   2160
Ala Asn Gln Leu Glu Arg Asn Gln Gly Tyr Lys Leu Val Val Phe Gly
675                 680                 685                 690 aaa ggt gca aca gct cct gtt aaa gat gct gca aat gca aat act tta   2208
Lys Gly Ala Thr Ala Pro Val Lys Asp Ala Ala Asn Ala Asn Thr Leu
                695                 700                 705 gca act aac tat atc tat aca ttt aca act gaa ggt caa gac gta aca   2256
Ala Thr Asn Tyr Ile Tyr Thr Phe Thr Thr Glu Gly Gln Asp Val Thr
            710                 715                 720 gca cca acg gtt aca aaa gta ttc aaa ggt gat tct tta aaa gac gct   2304
Ala Pro Thr Val Thr Lys Val Phe Lys Gly Asp Ser Leu Lys Asp Ala
            725                 730                 735 gat gca gtt act aca ctt acg aac gtt gat gca ggt caa aaa ttc act   2352
Asp Ala Val Thr Thr Leu Thr Asn Val Asp Ala Gly Gln Lys Phe Thr
            740                 745                 750 atc caa ttt agc gaa gaa tta aaa act tct agt ggt tct tta gtg ggt   2400
Ile Gln Phe Ser Glu Glu Leu Lys Thr Ser Ser Gly Ser Leu Val Gly
755                 760                 765                 770 ggc aaa gta act gtc gag aaa tta aca aac aac gga tgg gta gat gct   2448
Gly Lys Val Thr Val Glu Lys Leu Thr Asn Asn Gly Trp Val Asp Ala
                775                 780                 785 ggt act gga aca act gta tca gtt gct cct aag aca gat gca aat ggt   2496
Gly Thr Gly Thr Thr Val Ser Val Ala Pro Lys Thr Asp Ala Asn Gly
            790                 795                 800 aaa gta aca gct gct gtg gtt aca tta act ggt ctt gac aat aac gac   2544
Lys Val Thr Ala Ala Val Val Thr Leu Thr Gly Leu Asp Asn Asn Asp
            805                 810                 815 aaa gat gcg aaa ttg cgt ctg gta gta gat aag tct tct act gat gga   2592
Lys Asp Ala Lys Leu Arg Leu Val Val Asp Lys Ser Ser Thr Asp Gly
            820                 825                 830 att gct gat gta gct ggt aat gta att aag gaa aaa gat att tta att   2640
Ile Ala Asp Val Ala Gly Asn Val Ile Lys Glu Lys Asp Ile Leu Ile
835                 840                 845                 850 cgt tac aac agc tgg aga cac act gta gct tct gtg aaa gct gct gct   2688
Arg Tyr Asn Ser Trp Arg His Thr Val Ala Ser Val Lys Ala Ala Ala
                855                 860                 865 gac aaa gat ggt caa aac gct tct gct gca ttc cca aca agc act gca   2736
Asp Lys Asp Gly Gln Asn Ala Ser Ala Ala Phe Pro Thr Ser Thr Ala
            870                 875                 880
```

-continued

| | |
|---|---|
| att gat aca act aag agc tta tta gtt gaa ttc aat gaa act gat tta<br>Ile Asp Thr Thr Lys Ser Leu Leu Val Glu Phe Asn Glu Thr Asp Leu<br>     885                890              895 | 2784 |
| gcg gaa gtt aaa cct gag aac atc gtt gtt aaa gat gca gca ggt aat<br>Ala Glu Val Lys Pro Glu Asn Ile Val Val Lys Asp Ala Ala Gly Asn<br>900               905                910 | 2832 |
| gcg gta gct ggt act gta aca gca tta gac ggt tct aca aat aaa ttt<br>Ala Val Ala Gly Thr Val Thr Ala Leu Asp Gly Ser Thr Asn Lys Phe<br>915                920              925              930 | 2880 |
| gta ttc act cca tct caa gaa tta aaa gct ggt aca gtt tac tct gta<br>Val Phe Thr Pro Ser Gln Glu Leu Lys Ala Gly Thr Val Tyr Ser Val<br>     935               940              945 | 2928 |
| aca att gac ggt gtg aga gat aaa gta ggt aac aca atc tct aaa tac<br>Thr Ile Asp Gly Val Arg Asp Lys Val Gly Asn Thr Ile Ser Lys Tyr<br>     950               955              960 | 2976 |
| att act tcg ttc aag act gta tct gcg aat cca acg tta tct tca atc<br>Ile Thr Ser Phe Lys Thr Val Ser Ala Asn Pro Thr Leu Ser Ser Ile<br>     965               970              975 | 3024 |
| agc att gct gac ggt gca gtt aac gtt gac cgt tct aaa aca att aca<br>Ser Ile Ala Asp Gly Ala Val Asn Val Asp Arg Ser Lys Thr Ile Thr<br>980               985                990 | 3072 |
| att gaa ttc agc gat tca gtt cca aac cca aca atc act ctt aag aag<br>Ile Glu Phe Ser Asp Ser Val Pro Asn Pro Thr Ile Thr Leu Lys Lys<br>995             1000           1005           1010 | 3120 |
| gct gac gga act tca ttt act aat tac act tta gta aat gta aat aat<br>Ala Asp Gly Thr Ser Phe Thr Asn Tyr Thr Leu Val Asn Val Asn Asn<br>           1015           1020           1025 | 3168 |
| gaa aat aaa aca tac aaa att gta ttc cac aaa ggt gta aca ctt gac<br>Glu Asn Lys Thr Tyr Lys Ile Val Phe His Lys Gly Val Thr Leu Asp<br>           1030           1035           1040 | 3216 |
| gag ttt act caa tat gag tta gca gtt tca aaa gat ttt caa act ggt<br>Glu Phe Thr Gln Tyr Glu Leu Ala Val Ser Lys Asp Phe Gln Thr Gly<br>      1045           1050           1055 | 3264 |
| act gat att gat agc aaa gtt aca ttc atc aca ggt tct gtt gct act<br>Thr Asp Ile Asp Ser Lys Val Thr Phe Ile Thr Gly Ser Val Ala Thr<br>    1060           1065           1070 | 3312 |
| gac gaa gta aaa cct gct cta gta ggc gtt ggt tca tgg aat gga aca<br>Asp Glu Val Lys Pro Ala Leu Val Gly Val Gly Ser Trp Asn Gly Thr<br>1075           1080           1085           1090 | 3360 |
| agc tat act cag gat gct gca gca aca cga ctt cgg tct gta gct gac<br>Ser Tyr Thr Gln Asp Ala Ala Ala Thr Arg Leu Arg Ser Val Ala Asp<br>      1095           1100           1105 | 3408 |
| ttc gtt gcg gag cca gtt gcc ctt caa ttc tca gaa ggt atc gat tta<br>Phe Val Ala Glu Pro Val Ala Leu Gln Phe Ser Glu Gly Ile Asp Leu<br>           1110           1115           1120 | 3456 |
| acg aat gca act gtg aca gta aca aat att act gat gat aaa act gtt<br>Thr Asn Ala Thr Val Thr Val Thr Asn Ile Thr Asp Asp Lys Thr Val<br>    1125           1130           1135 | 3504 |
| gaa gtt att tca aaa gag agt gta gac gca gac cat gat gca ggt gct<br>Glu Val Ile Ser Lys Glu Ser Val Asp Ala Asp His Asp Ala Gly Ala<br>      1140           1145           1150 | 3552 |
| act aag gag aca tta gta att aac aca gtt act cct tta gta ctt gat<br>Thr Lys Glu Thr Leu Val Ile Asn Thr Val Thr Pro Leu Val Leu Asp<br>1155           1160           1165           1170 | 3600 |
| aac agc aag act tat aag att gtt gta agt gga gtt aaa gat gca gca<br>Asn Ser Lys Thr Tyr Lys Ile Val Val Ser Gly Val Lys Asp Ala Ala<br>      1175           1180           1185 | 3648 |
| ggt aat gtt gca gat act att aca ttc tat att aag taa<br>Gly Asn Val Ala Asp Thr Ile Thr Phe Tyr Ile Lys<br>           1190           1195 | 3687 |

<210> SEQ ID NO 2
<211> LENGTH: 1228
<212> TYPE: PRT
<213> ORGANISM: Bacillus stearothermophilus

<400> SEQUENCE: 2

```
Met Asp Arg Lys Lys Ala Val Lys Leu Ala Thr Ala Ser Ala Ile Ala
-30             -25                 -20                 -15

Ala Ser Ala Phe Val Ala Ala Asn Pro Asn Ala Ser Glu Ala Ala Thr
            -10                  -5                  -1   1

Asp Val Ala Thr Val Val Ser Gln Ala Lys Ala Gln Phe Lys Lys Ala
             5                  10                  15

Tyr Tyr Thr Tyr Ser His Thr Val Thr Glu Thr Gly Glu Phe Pro Asn
         20                  25                  30

Ile Asn Asp Val Tyr Ala Glu Tyr Asn Lys Ala Lys Lys Arg Tyr Arg
 35                  40                  45                  50

Asp Ala Val Ala Leu Val Asn Lys Ala Gly Ala Lys Lys Asp Ala
                 55                  60                  65

Tyr Leu Ala Asp Leu Gln Lys Glu Tyr Glu Thr Tyr Val Phe Lys Ala
             70                  75                  80

Asn Pro Lys Ser Gly Glu Ala Arg Val Ala Thr Tyr Ile Asp Ala Tyr
         85                  90                  95

Asn Tyr Ala Thr Lys Leu Asp Glu Met Arg Gln Glu Leu Glu Ala Ala
    100                 105                 110

Val Gln Ala Lys Asp Leu Glu Lys Ala Glu Gln Tyr Tyr His Lys Ile
115                 120                 125                 130

Pro Tyr Glu Ile Lys Thr Arg Thr Val Ile Leu Asp Arg Val Tyr Gly
                135                 140                 145

Lys Thr Thr Arg Asp Leu Leu Arg Ser Thr Phe Lys Ala Lys Ala Gln
                150                 155                 160

Glu Leu Arg Asp Ser Leu Ile Tyr Asp Ile Thr Val Ala Met Lys Ala
                165                 170                 175

Arg Glu Val Gln Asp Ala Val Lys Ala Gly Asn Leu Asp Lys Ala Lys
                180                 185                 190

Ala Ala Val Asp Gln Ile Asn Gln Tyr Leu Pro Lys Val Thr Asp Ala
195                 200                 205                 210

Phe Lys Thr Glu Leu Thr Glu Val Ala Lys Lys Ala Leu Asp Ala Asp
                215                 220                 225

Glu Ala Ala Leu Thr Pro Lys Val Glu Ser Val Ser Ala Ile Asn Thr
                230                 235                 240

Gln Asn Lys Ala Val Glu Leu Thr Ala Val Pro Val Asn Gly Thr Leu
                245                 250                 255

Lys Leu Gln Leu Ser Ala Ala Asn Glu Asp Thr Val Asn Val Asn
        260                 265                 270

Thr Val Arg Ile Tyr Lys Val Asp Gly Asn Ile Pro Phe Ala Leu Asn
275                 280                 285                 290

Thr Ala Asp Val Ser Leu Ser Thr Asp Gly Lys Thr Ile Thr Val Asp
                295                 300                 305

Ala Ser Thr Pro Phe Glu Asn Asn Thr Glu Tyr Lys Val Val Lys
                310                 315                 320

Gly Ile Lys Asp Lys Asn Gly Lys Glu Phe Lys Glu Asp Ala Phe Thr
                325                 330                 335

Phe Lys Leu Arg Asn Asp Ala Val Val Thr Gln Val Phe Gly Thr Asn
```

-continued

```
            340                 345                 350
Val Thr Asn Asn Thr Ser Val Asn Leu Ala Ala Gly Thr Phe Asp Thr
355                 360                 365                 370

Asp Asp Thr Leu Thr Val Val Phe Asp Lys Leu Leu Ala Pro Glu Thr
                375                 380                 385

Val Asn Ser Ser Asn Val Thr Ile Thr Asp Val Glu Thr Gly Lys Arg
                390                 395                 400

Ile Pro Val Ile Ala Ser Thr Ser Gly Ser Thr Ile Thr Ile Thr Leu
                405                 410                 415

Lys Glu Ala Leu Val Thr Gly Lys Gln Tyr Lys Leu Ala Ile Asn Asn
        420                 425                 430

Val Lys Thr Leu Thr Gly Tyr Asn Ala Glu Ala Tyr Glu Leu Val Phe
435                 440                 445                 450

Thr Ala Asn Ala Ser Ala Pro Thr Val Ala Thr Ala Pro Thr Thr Leu
                455                 460                 465

Gly Gly Thr Thr Leu Ser Thr Gly Ser Leu Thr Thr Asn Val Trp Gly
                470                 475                 480

Lys Leu Ala Gly Gly Val Asn Glu Ala Gly Thr Tyr Tyr Pro Gly Leu
        485                 490                 495

Gln Phe Thr Thr Thr Phe Ala Thr Lys Leu Asp Glu Ser Thr Leu Ala
    500                 505                 510

Asp Asn Phe Val Leu Val Glu Lys Glu Ser Gly Thr Val Val Ala Ser
515                 520                 525                 530

Glu Leu Lys Tyr Asn Ala Asp Ala Lys Met Val Thr Leu Val Pro Lys
                535                 540                 545

Ala Asp Leu Lys Glu Asn Thr Ile Tyr Gln Ile Lys Ile Lys Lys Gly
                550                 555                 560

Leu Lys Ser Asp Lys Gly Ile Glu Leu Gly Thr Val Asn Glu Lys Thr
                565                 570                 575

Tyr Glu Phe Lys Thr Gln Asp Leu Thr Ala Pro Thr Val Ile Ser Val
        580                 585                 590

Thr Ser Lys Asn Gly Asp Ala Gly Leu Lys Val Thr Glu Ala Gln Glu
595                 600                 605                 610

Phe Thr Val Lys Phe Ser Glu Asn Leu Asn Thr Phe Asn Ala Thr Thr
                615                 620                 625

Val Ser Gly Ser Thr Ile Thr Tyr Gly Gln Val Ala Val Lys Ala
                630                 635                 640

Gly Ala Asn Leu Ser Ala Leu Thr Ala Ser Asp Ile Ile Pro Ala Ser
        645                 650                 655

Val Glu Ala Val Thr Gly Gln Asp Gly Thr Tyr Lys Val Lys Val Ala
        660                 665                 670

Ala Asn Gln Leu Glu Arg Asn Gln Gly Tyr Lys Leu Val Val Phe Gly
675                 680                 685                 690

Lys Gly Ala Thr Ala Pro Val Lys Asp Ala Ala Asn Ala Asn Thr Leu
                695                 700                 705

Ala Thr Asn Tyr Ile Tyr Thr Phe Thr Thr Glu Gly Gln Asp Val Thr
                710                 715                 720

Ala Pro Thr Val Thr Lys Val Phe Lys Gly Asp Ser Leu Lys Asp Ala
                725                 730                 735

Asp Ala Val Thr Thr Leu Thr Asn Val Asp Ala Gly Gln Lys Phe Thr
        740                 745                 750

Ile Gln Phe Ser Glu Glu Leu Lys Thr Ser Ser Gly Ser Leu Val Gly
755                 760                 765                 770
```

-continued

```
Gly Lys Val Thr Val Glu Lys Leu Thr Asn Asn Gly Trp Val Asp Ala
            775                 780                 785

Gly Thr Gly Thr Thr Val Ser Val Ala Pro Lys Thr Asp Ala Asn Gly
            790                 795                 800

Lys Val Thr Ala Ala Val Val Thr Leu Thr Gly Leu Asp Asn Asn Asp
            805                 810                 815

Lys Asp Ala Lys Leu Arg Leu Val Val Asp Lys Ser Ser Thr Asp Gly
            820                 825                 830

Ile Ala Asp Val Ala Gly Asn Val Ile Lys Glu Lys Asp Ile Leu Ile
835                 840                 845                 850

Arg Tyr Asn Ser Trp Arg His Thr Val Ala Ser Val Lys Ala Ala Ala
            855                 860                 865

Asp Lys Asp Gly Gln Asn Ala Ser Ala Ala Phe Pro Thr Ser Thr Ala
            870                 875                 880

Ile Asp Thr Thr Lys Ser Leu Leu Val Glu Phe Asn Glu Thr Asp Leu
            885                 890                 895

Ala Glu Val Lys Pro Glu Asn Ile Val Val Lys Asp Ala Ala Gly Asn
            900                 905                 910

Ala Val Ala Gly Thr Val Thr Ala Leu Asp Gly Ser Thr Asn Lys Phe
915                 920                 925                 930

Val Phe Thr Pro Ser Gln Glu Leu Lys Ala Gly Thr Val Tyr Ser Val
            935                 940                 945

Thr Ile Asp Gly Val Arg Asp Lys Val Gly Asn Thr Ile Ser Lys Tyr
            950                 955                 960

Ile Thr Ser Phe Lys Thr Val Ser Ala Asn Pro Thr Leu Ser Ser Ile
            965                 970                 975

Ser Ile Ala Asp Gly Ala Val Asn Val Asp Arg Ser Lys Thr Ile Thr
            980                 985                 990

Ile Glu Phe Ser Asp Ser Val Pro Asn Pro Thr Ile Thr Leu Lys Lys
995                 1000                1005                1010

Ala Asp Gly Thr Ser Phe Thr Asn Tyr Thr Leu Val Asn Val Asn Asn
            1015                1020                1025

Glu Asn Lys Thr Tyr Lys Ile Val Phe His Lys Gly Val Thr Leu Asp
            1030                1035                1040

Glu Phe Thr Gln Tyr Glu Leu Ala Val Ser Lys Asp Phe Gln Thr Gly
            1045                1050                1055

Thr Asp Ile Asp Ser Lys Val Thr Phe Ile Thr Gly Ser Val Ala Thr
            1060                1065                1070

Asp Glu Val Lys Pro Ala Leu Val Gly Val Gly Ser Trp Asn Gly Thr
1075                1080                1085                1090

Ser Tyr Thr Gln Asp Ala Ala Ala Thr Arg Leu Arg Ser Val Ala Asp
            1095                1100                1105

Phe Val Ala Glu Pro Val Ala Leu Gln Phe Ser Glu Gly Ile Asp Leu
            1110                1115                1120

Thr Asn Ala Thr Val Thr Val Thr Asn Ile Thr Asp Asp Lys Thr Val
            1125                1130                1135

Glu Val Ile Ser Lys Glu Ser Val Asp Ala Asp His Asp Ala Gly Ala
            1140                1145                1150

Thr Lys Glu Thr Leu Val Ile Asn Thr Val Thr Pro Leu Val Leu Asp
1155                1160                1165                1170

Asn Ser Lys Thr Tyr Lys Ile Val Val Ser Gly Val Lys Asp Ala Ala
            1175                1180                1185
```

```
<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: synthetic
      primer

<400> SEQUENCE: 3
ttaatcgatt ctagatggat aggaaaaaag ctg                                    33

<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence: synthetic
      primer

<400> SEQUENCE: 4
atacccgggg gtacggatcc gatacagatt tgagcaa                                37

<210> SEQ ID NO 5
<211> LENGTH: 2766
<212> TYPE: DNA
<213> ORGANISM: Bacillus stearothermophilus
<220> FEATURE:
<221> NAME/KEY: CDS
<222> LOCATION: (1)..(2763)
<221> NAME/KEY: sig_peptide
<222> LOCATION: (1)..(93)
<221> NAME/KEY: mat_peptide
<222> LOCATION: (94)..(2763)

<400> SEQUENCE: 5
```

| | | | | | | | | | | | | | | | | |
|---|---|---|---|---|---|---|---|---|---|---|---|---|---|---|---|---|
| atg | gct | tat | caa | cct | aag | tct | ttt | cgc | aag | ttt | gtt | gcg | aca | act | gca | 48 |
| Met | Ala | Tyr | Gln | Pro | Lys | Ser | Phe | Arg | Lys | Phe | Val | Ala | Thr | Thr | Ala | |
| -30 | | | | | -25 | | | | | -20 | | | | | | |
| aca | gct | gcc | att | gta | gca | tct | gcg | gta | gct | cct | gta | gta | tct | gca | gca | 96 |
| Thr | Ala | Ala | Ile | Val | Ala | Ser | Ala | Val | Ala | Pro | Val | Val | Ser | Ala | Ala | |
| -15 | | | | -10 | | | | | -5 | | | | | -1 | 1 | |
| agc | ttc | aca | gat | gtt | gcg | ccg | caa | tat | aaa | gat | gcg | atc | gat | ttc | tta | 144 |
| Ser | Phe | Thr | Asp | Val | Ala | Pro | Gln | Tyr | Lys | Asp | Ala | Ile | Asp | Phe | Leu | |
| | | | 5 | | | | | 10 | | | | | 15 | | | |
| gta | tca | act | ggt | gca | aca | aaa | ggt | aaa | aca | gaa | aca | aaa | ttc | ggc | gtt | 192 |
| Val | Ser | Thr | Gly | Ala | Thr | Lys | Gly | Lys | Thr | Glu | Thr | Lys | Phe | Gly | Val | |
| | 20 | | | | | 25 | | | | | 30 | | | | | |
| tac | gat | gaa | atc | act | cgt | cta | gat | gcg | gca | gtt | att | ctt | gca | aga | gta | 240 |
| Tyr | Asp | Glu | Ile | Thr | Arg | Leu | Asp | Ala | Ala | Val | Ile | Leu | Ala | Arg | Val | |
| | 35 | | | | | 40 | | | | | 45 | | | | | |
| tta | aaa | cta | gac | gtt | gac | aac | gca | aaa | gac | gca | ggc | ttc | aca | gat | gtg | 288 |
| Leu | Lys | Leu | Asp | Val | Asp | Asn | Ala | Lys | Asp | Ala | Gly | Phe | Thr | Asp | Val | |
| 50 | | | | | 55 | | | | | 60 | | | | | 65 | |
| cca | aaa | gac | cgt | gca | aaa | tac | gtc | aac | gcg | ctt | gta | gaa | gct | ggc | gta | 336 |
| Pro | Lys | Asp | Arg | Ala | Lys | Tyr | Val | Asn | Ala | Leu | Val | Glu | Ala | Gly | Val | |
| | | | 70 | | | | | 75 | | | | | 80 | | | |
| tta | aac | ggt | aaa | gca | cct | ggc | aaa | ttt | ggt | gca | tac | gac | cca | tta | act | 384 |
| Leu | Asn | Gly | Lys | Ala | Pro | Gly | Lys | Phe | Gly | Ala | Tyr | Asp | Pro | Leu | Thr | |
| | | 85 | | | | | 90 | | | | | 95 | | | | |
| cgc | gtt | gaa | atg | gca | aaa | atc | atc | gcg | aac | cgt | tac | aaa | tta | aaa | gct | 432 |
| Arg | Val | Glu | Met | Ala | Lys | Ile | Ile | Ala | Asn | Arg | Tyr | Lys | Leu | Lys | Ala | |
| | | 100 | | | | | 105 | | | | | 110 | | | | |

```
gac gat gta aaa ctt cca ttc act gat gta aac gat aca tgg gca cca    480
Asp Asp Val Lys Leu Pro Phe Thr Asp Val Asn Asp Thr Trp Ala Pro
115                 120                 125 tac gta aaa gcg ctt tat aaa tac gaa gta acc aaa agg tta aaa cac    528
Tyr Val Lys Ala Leu Tyr Lys Tyr Glu Val Thr Lys Arg Leu Lys His
130                 135                 140                 145 caa caa gct tcg gtg cat acc aaa aac atc act ctg cgt gac ttt gcg    576
Gln Gln Ala Ser Val His Thr Lys Asn Ile Thr Leu Arg Asp Phe Ala
                150                 155                 160 caa ttt gta tat aga gcg gtg aat att aat gca gtg cca gaa ata gtt    624
Gln Phe Val Tyr Arg Ala Val Asn Ile Asn Ala Val Pro Glu Ile Val
                165                 170                 175 gaa gta act gcg gtt aat tcg act aca gtg aaa gta aca ttc aat acg    672
Glu Val Thr Ala Val Asn Ser Thr Thr Val Lys Val Thr Phe Asn Thr
                180                 185                 190 caa att gct gat gtt gat ttc aca aat ttt gct atc gat aac ggt tta    720
Gln Ile Ala Asp Val Asp Phe Thr Asn Phe Ala Ile Asp Asn Gly Leu
195                 200                 205 act gtt act aaa gca act ctt tct cgt gat aaa aaa tcc gta gag gtt    768
Thr Val Thr Lys Ala Thr Leu Ser Arg Asp Lys Lys Ser Val Glu Val
210                 215                 220                 225 gtg gta aat aaa ccg ttt act cgt aat cag gaa tat aca att aca gcg    816
Val Val Asn Lys Pro Phe Thr Arg Asn Gln Glu Tyr Thr Ile Thr Ala
                230                 235                 240 aca ggc att aaa aat tta aaa ggc gag acc gct aag gaa tta act ggt    864
Thr Gly Ile Lys Asn Leu Lys Gly Glu Thr Ala Lys Glu Leu Thr Gly
                245                 250                 255 aag ttt gtt tgg tct gtt caa gat gcg gta act gtt gca cta aat aat    912
Lys Phe Val Trp Ser Val Gln Asp Ala Val Thr Val Ala Leu Asn Asn
                260                 265                 270 agt tcg ctt aaa gtt gga gag gaa tct ggt tta act gta aaa gat cag    960
Ser Ser Leu Lys Val Gly Glu Glu Ser Gly Leu Thr Val Lys Asp Gln
275                 280                 285 gat ggc aaa gat gtt gta ggt gct aaa gta gaa ctt act tct tct aat    1008
Asp Gly Lys Asp Val Val Gly Ala Lys Val Glu Leu Thr Ser Ser Asn
290                 295                 300                 305 act aat att gtt gta gtt tca agt ggc gaa gta tca gta tct gct gct    1056
Thr Asn Ile Val Val Val Ser Ser Gly Glu Val Ser Val Ser Ala Ala
                310                 315                 320 aaa gtt aca gct gta aaa ccg gga aca gct gat gtt act gca aaa gtt    1104
Lys Val Thr Ala Val Lys Pro Gly Thr Ala Asp Val Thr Ala Lys Val
                325                 330                 335 aca tta cca gat ggt gtt gta cta aca aat aca ttt aaa gtg aca gtt    1152
Thr Leu Pro Asp Gly Val Val Leu Thr Asn Thr Phe Lys Val Thr Val
                340                 345                 350 aca gaa gtg cct gtt caa gtc caa aat caa gga ttt act tta gtt gat    1200
Thr Glu Val Pro Val Gln Val Gln Asn Gln Gly Phe Thr Leu Val Asp
355                 360                 365 aat ctt tct aat gct cca cag aat aca gtt gca ttt aac aaa gct gag    1248
Asn Leu Ser Asn Ala Pro Gln Asn Thr Val Ala Phe Asn Lys Ala Glu
370                 375                 380                 385 aaa gta act tca atg ttt gct gga gaa act aaa aca gtt gca atg tat    1296
Lys Val Thr Ser Met Phe Ala Gly Glu Thr Lys Thr Val Ala Met Tyr
                390                 395                 400 gat act aaa aac ggt gat cct gaa act aaa cct gtt gat ttc aaa gat    1344
Asp Thr Lys Asn Gly Asp Pro Glu Thr Lys Pro Val Asp Phe Lys Asp
                405                 410                 415 gca act gta cgt tca tta aat cca att att gca aca gct gct att aat    1392
Ala Thr Val Arg Ser Leu Asn Pro Ile Ile Ala Thr Ala Ala Ile Asn
```

```
                420                     425                     430
ggt agt gag ctc ctt gtc aca gct aat gct ggc caa tct gga aaa gct       1440
Gly Ser Glu Leu Leu Val Thr Ala Asn Ala Gly Gln Ser Gly Lys Ala
    435                     440                     445 tca ttt gaa gta aca tta aaa gat aat aca aaa aga aca ttt aca gtt       1488
Ser Phe Glu Val Thr Leu Lys Asp Asn Thr Lys Arg Thr Phe Thr Val
450                     455                     460                 465 gat gta aaa aaa gac cct gta tta caa gat ata aaa gta gat gca act       1536
Asp Val Lys Lys Asp Pro Val Leu Gln Asp Ile Lys Val Asp Ala Thr
                470                     475                     480 tct gtt aaa ctt tcc gat gaa gct gtt ggc ggc ggg gaa gtt gaa gga       1584
Ser Val Lys Leu Ser Asp Glu Ala Val Gly Gly Gly Glu Val Glu Gly
            485                     490                     495 gtt aac caa aaa acg att aaa gta agt gca gtt gac caa tac ggt aaa       1632
Val Asn Gln Lys Thr Ile Lys Val Ser Ala Val Asp Gln Tyr Gly Lys
        500                     505                     510 gaa att aaa ttt ggt aca aaa ggt aaa gtt act gtt aca act aat aca       1680
Glu Ile Lys Phe Gly Thr Lys Gly Lys Val Thr Val Thr Thr Asn Thr
    515                     520                     525 gaa gga cta gtt att aaa aat gta aat agc gat aat aca att gac ttt       1728
Glu Gly Leu Val Ile Lys Asn Val Asn Ser Asp Asn Thr Ile Asp Phe
530                     535                     540                 545 gat agc ggc aat agt gca act gac caa ttt gtt gtc gtt gca aca aaa       1776
Asp Ser Gly Asn Ser Ala Thr Asp Gln Phe Val Val Val Ala Thr Lys
                550                     555                     560 gac aaa att gtc aat ggt aaa gta gaa gtt aaa tat ttc aaa aat gct       1824
Asp Lys Ile Val Asn Gly Lys Val Glu Val Lys Tyr Phe Lys Asn Ala
            565                     570                     575 agt gac aca aca cca act tca act aaa aca att act gtt aat gta gta       1872
Ser Asp Thr Thr Pro Thr Ser Thr Lys Thr Ile Thr Val Asn Val Val
        580                     585                     590 aat gta aaa gct gac gct aca cca gta gga tta gat att gta gca cct       1920
Asn Val Lys Ala Asp Ala Thr Pro Val Gly Leu Asp Ile Val Ala Pro
    595                     600                     605 tct aaa att gat gta aat gct cca aac act gct tct act gca gat gtt       1968
Ser Lys Ile Asp Val Asn Ala Pro Asn Thr Ala Ser Thr Ala Asp Val
610                     615                     620                 625 gat ttt ata aat ttc gaa agt gtt gag att tac aca ctc gat tca aat       2016
Asp Phe Ile Asn Phe Glu Ser Val Glu Ile Tyr Thr Leu Asp Ser Asn
                630                     635                     640 ggt aga cgt caa aaa aaa gtt act cca act gca act aca ctt gta ggt       2064
Gly Arg Arg Gln Lys Lys Val Thr Pro Thr Ala Thr Thr Leu Val Gly
            645                     650                     655 aca aaa aaa aaa aaa aaa gtt aat ggg aat gta tta caa ttc aag ggg       2112
Thr Lys Lys Lys Lys Lys Val Asn Gly Asn Val Leu Gln Phe Lys Gly
        660                     665                     670 aac gaa gaa tta acg cta tca act tct tct agt aca gga aac gta gat       2160
Asn Glu Glu Leu Thr Leu Ser Thr Ser Ser Ser Thr Gly Asn Val Asp
    675                     680                     685 gga aca gca gaa gga atg aca aaa cgt att cca ggg aaa tat atc aac       2208
Gly Thr Ala Glu Gly Met Thr Lys Arg Ile Pro Gly Lys Tyr Ile Asn
690                     695                     700                 705 tct gca agt gta cct gcc agt gca aca gta gca aca agt cct gtt act       2256
Ser Ala Ser Val Pro Ala Ser Ala Thr Val Ala Thr Ser Pro Val Thr
                710                     715                     720 gta aag ctt aat tca agt gat aat gat tta aca ttt gaa gaa tta ata       2304
Val Lys Leu Asn Ser Ser Asp Asn Asp Leu Thr Phe Glu Glu Leu Ile
            725                     730                     735 ttc ggt gta att gac cct aca caa tta gtc aaa gat gaa gac atc aac       2352
```

```
                                                                           -continued Phe Gly Val Ile Asp Pro Thr Gln Leu Val Lys Asp Glu Asp Ile Asn
        740                 745                 750 gaa ttt att gca gtt tca aaa gcg gct aaa aat gat gga tat ttg tat           2400
Glu Phe Ile Ala Val Ser Lys Ala Ala Lys Asn Asp Gly Tyr Leu Tyr
755                 760                 765 aat aaa ccg ctt gta acg gtt aaa gat gca tca gga aaa gtt att cca           2448
Asn Lys Pro Leu Val Thr Val Lys Asp Ala Ser Gly Lys Val Ile Pro
770                 775                 780                 785 aca ggt gca aat gtt tac ggt cta aat cat gat gca act aac gga aac           2496
Thr Gly Ala Asn Val Tyr Gly Leu Asn His Asp Ala Thr Asn Gly Asn
                790                 795                 800 att tgg ttt gat gag gaa caa gct ggc tta gct aaa aaa ttt agt gat           2544
Ile Trp Phe Asp Glu Glu Gln Ala Gly Leu Ala Lys Lys Phe Ser Asp
        805                 810                 815 gta cat ttt gat gtt gat ttt tca tta act aac gtt gta aaa act ggt           2592
Val His Phe Asp Val Asp Phe Ser Leu Thr Asn Val Val Lys Thr Gly
820                 825                 830 agc ggt aca gtt tct tca tcg cca tca tta tct gac gca att caa ctt           2640
Ser Gly Thr Val Ser Ser Ser Pro Ser Leu Ser Asp Ala Ile Gln Leu
835                 840                 845 act aat tca ggc gat gca gta tcg ttt aca tta gtt atc aaa tca att           2688
Thr Asn Ser Gly Asp Ala Val Ser Phe Thr Leu Val Ile Lys Ser Ile
850                 855                 860                 865 tat gtt aaa ggc gca gat aaa gat gat aat aac tta ctt gca gcc cct           2736
Tyr Val Lys Gly Ala Asp Lys Asp Asp Asn Asn Leu Leu Ala Ala Pro
                870                 875                 880 gtt tct gtc aat gtg act gtg aca aaa taa                                   2766
Val Ser Val Asn Val Thr Val Thr Lys
        885                 890

<210> SEQ ID NO 6
<211> LENGTH: 921
<212> TYPE: PRT
<213> ORGANISM: Bacillus stearothermophilus

<400> SEQUENCE: 6

Met Ala Tyr Gln Pro Lys Ser Phe Arg Lys Phe Val Ala Thr Thr Ala
    -30                 -25                 -20

Thr Ala Ala Ile Val Ala Ser Ala Val Ala Pro Val Val Ser Ala Ala
-15                 -10                  -5                  -1   1

Ser Phe Thr Asp Val Ala Pro Gln Tyr Lys Asp Ala Ile Asp Phe Leu
                  5                  10                  15

Val Ser Thr Gly Ala Thr Lys Gly Lys Thr Glu Thr Lys Phe Gly Val
            20                  25                  30

Tyr Asp Glu Ile Thr Arg Leu Asp Ala Ala Val Ile Leu Ala Arg Val
        35                  40                  45

Leu Lys Leu Asp Val Asp Asn Ala Lys Asp Ala Gly Phe Thr Asp Val
50                  55                  60                  65

Pro Lys Asp Arg Ala Lys Tyr Val Asn Ala Leu Val Glu Ala Gly Val
                70                  75                  80

Leu Asn Gly Lys Ala Pro Gly Lys Phe Gly Ala Tyr Asp Pro Leu Thr
            85                  90                  95

Arg Val Glu Met Ala Lys Ile Ile Ala Asn Arg Tyr Lys Leu Lys Ala
        100                 105                 110

Asp Asp Val Lys Leu Pro Phe Thr Asp Val Asn Asp Thr Trp Ala Pro
115                 120                 125

Tyr Val Lys Ala Leu Tyr Lys Tyr Glu Val Thr Lys Arg Leu Lys His
130                 135                 140                 145
```

-continued

```
Gln Gln Ala Ser Val His Thr Lys Asn Ile Thr Leu Arg Asp Phe Ala
            150                 155                 160
Gln Phe Val Tyr Arg Ala Val Asn Ile Asn Ala Val Pro Glu Ile Val
            165                 170                 175
Glu Val Thr Ala Val Asn Ser Thr Thr Val Lys Val Thr Phe Asn Thr
            180                 185                 190
Gln Ile Ala Asp Val Asp Phe Thr Asn Phe Ala Ile Asp Asn Gly Leu
            195                 200                 205
Thr Val Thr Lys Ala Thr Leu Ser Arg Asp Lys Lys Ser Val Glu Val
210                 215                 220                 225
Val Val Asn Lys Pro Phe Thr Arg Asn Gln Glu Tyr Thr Ile Thr Ala
            230                 235                 240
Thr Gly Ile Lys Asn Leu Lys Gly Glu Thr Ala Lys Glu Leu Thr Gly
            245                 250                 255
Lys Phe Val Trp Ser Val Gln Asp Ala Val Thr Val Ala Leu Asn Asn
            260                 265                 270
Ser Ser Leu Lys Val Gly Glu Glu Ser Gly Leu Thr Val Lys Asp Gln
275                 280                 285
Asp Gly Lys Asp Val Val Gly Ala Lys Val Glu Leu Thr Ser Ser Asn
290                 295                 300                 305
Thr Asn Ile Val Val Ser Ser Gly Glu Val Ser Val Ser Ala Ala
            310                 315                 320
Lys Val Thr Ala Val Lys Pro Gly Thr Ala Asp Val Thr Ala Lys Val
            325                 330                 335
Thr Leu Pro Asp Gly Val Val Leu Thr Asn Thr Phe Lys Val Thr Val
            340                 345                 350
Thr Glu Val Pro Val Gln Val Gln Asn Gln Gly Phe Thr Leu Val Asp
            355                 360                 365
Asn Leu Ser Asn Ala Pro Gln Asn Thr Val Ala Phe Asn Lys Ala Glu
370                 375                 380                 385
Lys Val Thr Ser Met Phe Ala Gly Glu Thr Lys Thr Val Ala Met Tyr
            390                 395                 400
Asp Thr Lys Asn Gly Asp Pro Glu Thr Lys Pro Val Asp Phe Lys Asp
            405                 410                 415
Ala Thr Val Arg Ser Leu Asn Pro Ile Ile Ala Thr Ala Ala Ile Asn
            420                 425                 430
Gly Ser Glu Leu Leu Val Thr Ala Asn Ala Gly Gln Ser Gly Lys Ala
            435                 440                 445
Ser Phe Glu Val Thr Leu Lys Asp Asn Thr Lys Arg Thr Phe Thr Val
450                 455                 460                 465
Asp Val Lys Lys Asp Pro Val Leu Gln Asp Ile Lys Val Asp Ala Thr
            470                 475                 480
Ser Val Lys Leu Ser Asp Glu Ala Val Gly Gly Glu Val Glu Gly
            485                 490                 495
Val Asn Gln Lys Thr Ile Lys Val Ser Ala Val Asp Gln Tyr Gly Lys
            500                 505                 510
Glu Ile Lys Phe Gly Thr Lys Gly Lys Val Thr Val Thr Thr Asn Thr
            515                 520                 525
Glu Gly Leu Val Ile Lys Asn Val Asn Ser Asp Asn Thr Ile Asp Phe
530                 535                 540                 545
Asp Ser Gly Asn Ser Ala Thr Asp Gln Phe Val Val Ala Thr Lys
            550                 555                 560
```

Asp Lys Ile Val Asn Gly Lys Val Glu Val Lys Tyr Phe Lys Asn Ala
         565                 570                 575
Ser Asp Thr Thr Pro Thr Ser Thr Lys Thr Ile Thr Val Asn Val Val
         580                 585                 590
Asn Val Lys Ala Asp Ala Thr Pro Val Gly Leu Asp Ile Val Ala Pro
595                 600                 605
Ser Lys Ile Asp Val Asn Ala Pro Asn Thr Ala Ser Thr Ala Asp Val
610                 615                 620                 625
Asp Phe Ile Asn Phe Glu Ser Val Glu Ile Tyr Thr Leu Asp Ser Asn
             630                 635                 640
Gly Arg Arg Gln Lys Lys Val Thr Pro Thr Ala Thr Thr Leu Val Gly
         645                 650                 655
Thr Lys Lys Lys Lys Val Asn Gly Asn Val Leu Gln Phe Lys Gly
         660                 665                 670
Asn Glu Glu Leu Thr Leu Ser Thr Ser Ser Thr Gly Asn Val Asp
675                 680                 685
Gly Thr Ala Glu Gly Met Thr Lys Arg Ile Pro Gly Lys Tyr Ile Asn
690                 695                 700                 705
Ser Ala Ser Val Pro Ala Ser Ala Thr Val Ala Thr Ser Pro Val Thr
             710                 715                 720
Val Lys Leu Asn Ser Ser Asp Asn Asp Leu Thr Phe Glu Glu Leu Ile
         725                 730                 735
Phe Gly Val Ile Asp Pro Thr Gln Leu Val Lys Asp Glu Asp Ile Asn
             740                 745                 750
Glu Phe Ile Ala Val Ser Lys Ala Ala Lys Asn Asp Gly Tyr Leu Tyr
         755                 760                 765
Asn Lys Pro Leu Val Thr Val Lys Asp Ala Ser Gly Lys Val Ile Pro
770                 775                 780                 785
Thr Gly Ala Asn Val Tyr Gly Leu Asn His Asp Ala Thr Asn Gly Asn
             790                 795                 800
Ile Trp Phe Asp Glu Glu Gln Ala Gly Leu Ala Lys Lys Phe Ser Asp
             805                 810                 815
Val His Phe Asp Val Asp Phe Ser Leu Thr Asn Val Val Lys Thr Gly
         820                 825                 830
Ser Gly Thr Val Ser Ser Pro Ser Leu Ser Asp Ala Ile Gln Leu
         835                 840                 845
Thr Asn Ser Gly Asp Ala Val Ser Phe Thr Leu Val Ile Lys Ser Ile
850                 855                 860                 865
Tyr Val Lys Gly Ala Asp Lys Asp Asn Asn Leu Leu Ala Ala Pro
             870                 875                 880
Val Ser Val Asn Val Thr Val Thr Lys
         885                 890

<210> SEQ ID NO 7
<211> LENGTH: 498
<212> TYPE: DNA
<213> ORGANISM: Unknown Organism
<220> FEATURE:
<223> OTHER INFORMATION: Description of Unknown Organism: streptavidin
      gene

<400> SEQUENCE: 7
cccatggacc cgtccaagga ctccaaagct caggtttctg cagccgaagc tggtatcact    60
ggcacctggt ataaccaact ggggtcgact ttcattgtga ccgctggtgc ggacggagct   120
ctgactggca cctacgaatc tgcggttggt aacgcagaat cccgctacgt actgactggc   180

```
cgttatgact ctgcacctgc caccgatggc tctggtaccg ctctgggctg gactgtggct        240
tggaaaaaca actatcgtaa tgcgcacagc gccactacgt ggtctggcca atacgttggc        300
ggtgctgagg ctcgtatcaa cactcagtgg ctgttaacat ccggcactac cgaagcgaat        360
gcatggaaat cgacactagt aggtcatgac acctttacca aagttaagcc ttctgctgct        420
agcattgatg ctgccaagaa agcaggcgta aacaacggta accctctaga cgctgttcag        480
caataataag gatccggg                                                      498

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: synthetic
      primer

<400> SEQUENCE: 8
ttcatcgtaa acgccgaatt ttgtttctg                                          29

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: synthetic
      primer

<400> SEQUENCE: 9
agggaaatat atcaactctg caagtg                                             26

<210> SEQ ID NO 10
<211> LENGTH: 49
<212> TYPE: DNA
<213> ORGANISM: Bacillus stearothermophilus

<400> SEQUENCE: 10
gaattcatcg atgtcgacca aggaggtcta gatggatccg gccaagctt                    49
```